(12) United States Patent
Stowell et al.

(10) Patent No.: US 11,137,368 B2
(45) Date of Patent: Oct. 5, 2021

(54) RESONANT GAS SENSOR

(71) Applicant: Lyten, Inc., Sunnyvale, CA (US)

(72) Inventors: Michael W. Stowell, Sunnyvale, CA (US); Bruce Lanning, Littleton, CO (US); Sung H. Lim, Mountain View, CA (US); Shreeyukta Singh, San Jose, CA (US); John Chmiola, San Francisco, CA (US)

(73) Assignee: LytEn, Inc., San Jose, CA (US)

( * ) Notice: Subject to any disclaimer, the term of this patent is extended or adjusted under 35 U.S.C. 154(b) by 0 days.

(21) Appl. No.: 16/887,293

(22) Filed: May 29, 2020

(65) Prior Publication Data

US 2020/0292487 A1    Sep. 17, 2020

Related U.S. Application Data

(63) Continuation-in-part of application No. 16/706,542, filed on Dec. 6, 2019, now Pat. No. 10,955,378, (Continued)

(51) Int. Cl.
*G01N 27/414* (2006.01)
*C01B 32/182* (2017.01)
(Continued)

(52) U.S. Cl.
CPC .... *G01N 27/4141* (2013.01); *B01J 20/28066* (2013.01); *C01B 32/182* (2017.08); (Continued)

(58) Field of Classification Search
CPC ............ B01J 20/28066; C01B 32/182; G01N 27/4141; G01N 2291/014; G01N 27/127; (Continued)

(56) References Cited

U.S. PATENT DOCUMENTS 4,141,800 A * 2/1979 Breuer ............... G01N 27/4045
                                                    205/779.5
5,520,789 A    5/1996 Takahashi et al.
(Continued)

FOREIGN PATENT DOCUMENTS

CN        104677879 B    6/2017
WO    2000/014518 A1    3/2000
(Continued)

OTHER PUBLICATIONS

Alexander Y. Zhu, et al., "Optoelectromechanical Multimodal Biosensor with Graphene Active Region", NanoLetters, Sep. 3, 2014. (Year: 2014).*

(Continued)

*Primary Examiner* — David A. Rogers
(74) *Attorney, Agent, or Firm* — Paradice & Li LLP

(57) ABSTRACT

This disclosure provides a sensor for detecting an analyte. The sensor can include an antenna and sensing material both disposed on a substrate, where the sensing is electrically coupled to the antenna. The sensing material can include a carbon structure including a multi-modal distribution of pore sizes that define a surface area including bonding sites configured to interact with one or more additives and the analyte. The carbon structure is configured to generate a resonant signal indicative of one or more characteristics of the analyte in response to an electromagnetic signal. The carbon structure can include distinctly sized interconnected channels defined by the surface area and configured to be infiltrated by the analyte, and exposed surfaces configured to adsorb the analyte. Each of the interconnected channels can include microporous pathways and/or mesoporous pathways, which can increase a responsiveness of the sensing material proportionate to the analyte within the carbon structure.

26 Claims, 15 Drawing Sheets

Related U.S. Application Data which is a continuation of application No. 16/239,423, filed on Jan. 3, 2019, now Pat. No. 10,502,705.

(60) Provisional application No. 62/815,927, filed on Mar. 8, 2019, provisional application No. 62/613,716, filed on Jan. 4, 2018.

(51) Int. Cl.

| | | |
|---|---|---|
| *B01J 20/28* | (2006.01) | |
| *G01N 33/00* | (2006.01) | |
| *G01N 27/404* | (2006.01) | |
| *G01N 27/12* | (2006.01) | |
| *G01N 29/036* | (2006.01) | |

(52) U.S. Cl.
CPC ...... *C01B 2204/04* (2013.01); *C01B 2204/22* (2013.01); *C01B 2204/32* (2013.01); *G01N 27/127* (2013.01); *G01N 27/4045* (2013.01); *G01N 29/036* (2013.01); *G01N 33/004* (2013.01); *G01N 33/0037* (2013.01); *G01N 33/0039* (2013.01); *G01N 33/0044* (2013.01); *G01N 2291/014* (2013.01)

(58) Field of Classification Search
CPC ............. G01N 33/004; G01N 27/4045; G01N 29/036; G01N 33/0037; G01N 33/0039; G01N 33/0044
See application file for complete search history.

(56) References Cited

U.S. PATENT DOCUMENTS

| | | | |
|---|---|---|---|
| 5,725,754 A | 3/1998 | Belford | |
| 6,359,444 B1 | 3/2002 | Grimes | |
| 6,997,039 B2 | 2/2006 | Rao et al. | |
| 8,052,932 B2 * | 11/2011 | Han | B82Y 15/00 |
| | | | 422/90 |
| 8,281,642 B2 | 10/2012 | Lee et al. | |
| 8,364,419 B2 * | 1/2013 | Potyrailo | G01N 27/026 |
| | | | 702/24 |
| 8,567,232 B2 | 10/2013 | Ackley et al. | |
| 8,736,425 B2 | 5/2014 | Potyrailo | |
| 8,754,454 B2 | 6/2014 | Bryant et al. | |
| 8,877,370 B2 | 11/2014 | Kim | |
| 9,038,443 B1 | 5/2015 | Pace et al. | |
| 9,063,079 B2 | 6/2015 | Eckhardt et al. | |
| 9,088,054 B2 | 7/2015 | Lukso et al. | |
| 9,267,993 B2 | 2/2016 | Farmer et al. | |
| 9,304,102 B2 | 4/2016 | Day et al. | |
| 9,346,680 B2 * | 5/2016 | Liu | H01M 4/926 |
| 9,395,343 B2 | 7/2016 | Schmid et al. | |
| 9,612,690 B2 | 4/2017 | Zirkl et al. | |
| 9,678,036 B2 | 6/2017 | Balandin | |
| 9,705,469 B2 * | 7/2017 | Rinaldi | H03H 3/02 |
| 9,735,279 B2 | 8/2017 | Sato et al. | |
| 9,869,651 B2 | 1/2018 | Akinwande et al. | |
| 9,927,390 B2 | 3/2018 | Satou | |
| 10,024,831 B2 * | 7/2018 | Ruhl | G01N 33/004 |
| 10,031,097 B1 | 7/2018 | Han et al. | |
| 10,151,037 B2 * | 12/2018 | Hoeprich, Jr. | C25B 9/00 |
| 10,502,705 B2 | 12/2019 | Stowell et al. | |
| 10,802,018 B2 * | 10/2020 | Cubukcu | G01N 29/022 |
| 2001/0020383 A1 | 9/2001 | Moos et al. | |
| 2007/0048181 A1 | 3/2007 | Chang et al. | |
| 2007/0056352 A1 | 3/2007 | Birkhofer et al. | |
| 2007/0090926 A1 * | 4/2007 | Potyrailo | G01N 27/3275 |
| | | | 340/10.41 |
| 2008/0135614 A1 | 6/2008 | Werner et al. | |
| 2009/0145233 A1 | 6/2009 | Eklund et al. | |
| 2009/0327188 A1 * | 12/2009 | Ryhanen | G06K 9/00986 |
| | | | 706/46 |
| 2012/0006102 A1 | 1/2012 | Bryant et al. | |
| 2012/0049864 A1 * | 3/2012 | Han | G01N 27/127 |
| | | | 324/649 |
| 2012/0235690 A1 * | 9/2012 | Potyrailo | G01N 27/028 |
| | | | 324/652 |
| 2013/0040397 A1 | 2/2013 | Star et al. | |
| 2013/0214875 A1 * | 8/2013 | Duncan | B82Y 40/00 |
| | | | 333/186 |
| 2014/0260547 A1 * | 9/2014 | Balandin | B82Y 15/00 |
| | | | 73/31.06 |
| 2014/0305191 A1 | 10/2014 | Schmid et al. | |
| 2014/0336952 A1 | 11/2014 | Kellaway et al. | |
| 2015/0008486 A1 | 1/2015 | Bryant et al. | |
| 2015/0123678 A1 * | 5/2015 | Neikirk | G01N 27/04 |
| | | | 324/636 |
| 2015/0377824 A1 * | 12/2015 | Ruhl | G01N 27/127 |
| | | | 204/424 |
| 2016/0065169 A1 * | 3/2016 | Rinaldi | H03H 3/02 |
| | | | 250/338.3 |
| 2016/0091447 A1 | 3/2016 | Yu et al. | |
| 2016/0123947 A1 | 5/2016 | Briman et al. | |
| 2016/0161388 A1 * | 6/2016 | Niedermayer | G01N 29/036 |
| | | | 73/54.41 |
| 2016/0169824 A1 | 6/2016 | Shin et al. | |
| 2016/0177387 A1 * | 6/2016 | Roy | C12Q 2563/137 |
| | | | 435/6.1 |
| 2016/0195488 A1 | 7/2016 | Ensor et al. | |
| 2016/0282312 A1 | 9/2016 | Cable et al. | |
| 2016/0290956 A1 | 10/2016 | Sato et al. | |
| 2016/0377611 A1 * | 12/2016 | Ma | G01N 33/5438 |
| | | | 422/69 |
| 2017/0181669 A1 | 6/2017 | Lin et al. | |
| 2017/0236726 A1 * | 8/2017 | Jeong | H01L 21/68764 |
| | | | 438/747 |
| 2017/0276634 A1 | 9/2017 | Saffell et al. | |
| 2017/0315075 A1 * | 11/2017 | Akinwande | G01N 27/125 |
| 2017/0322094 A1 * | 11/2017 | Kim | G06F 3/044 |
| 2017/0330004 A1 | 11/2017 | Gibson | |
| 2017/0350882 A1 | 12/2017 | Lin et al. | |
| 2017/0356869 A1 | 12/2017 | Koenig et al. | |
| 2018/0059080 A1 | 3/2018 | Jun et al. | |
| 2018/0136157 A1 | 5/2018 | Harada et al. | |
| 2018/0275088 A1 * | 9/2018 | Huff | G01N 33/54326 |
| 2019/0064143 A1 | 2/2019 | Haick et al. | |
| 2019/0072510 A1 * | 3/2019 | Tai | H01L 51/0048 |
| 2019/0277702 A1 * | 9/2019 | Aleman | G01J 5/20 |
| 2019/0312171 A1 * | 10/2019 | Karabiyik | H01L 31/028 |
| 2020/0080977 A1 * | 3/2020 | Isobayashi | G01N 1/4005 |
| 2020/0244243 A1 | 7/2020 | Cullinan et al. | |
| 2020/0292487 A1 | 9/2020 | Stowell et al. | |

FOREIGN PATENT DOCUMENTS

| | | | | |
|---|---|---|---|---|
| WO | 2015/083073 A1 | 6/2015 | | |
| WO | WO-2015083073 A1 * | 6/2015 | ........... | H03H 9/2463 |
| WO | WO-2019067488 A1 * | 4/2019 | ........... | G01N 29/036 |
| WO | 2019/136181 A1 | 7/2019 | | |

OTHER PUBLICATIONS

Dossi et al., "An electrochemical gas sensor based on paper supported room temperature ionic liquids", Lab on a Chip, vol. 12, No. 1, Suppl. 1, Part 3, Feb. 2012, pp. 153-158.

International Search Report and Written Opinion dated Apr. 26, 2019 for PCT Patent Application No. PCT/US2019/012224, 9 pages.

Potyrailo, Radislav A., et al., "Multivariable MHz and GHz Wireless Chem/Bio Sensors for Environmental, Industrial, and Security Applications," IMCS May 2012, The 14th International Meeting on Chemical Sensors, pp. 399-402.

Sekhar et al., "Chemical Sensors for Environmental Monitoring and Homeland Security," The Electrochemical Society Interface, Winter 2010, pp. 35-40.

Singh, G., et al., "ZnO decorated luminescent graphene as a potential gas sensor at room temperature", Carbon, vol. 50, avail. from ScienceDirect on Sep. 1, 2011, pp. 385-394.

(56) References Cited

OTHER PUBLICATIONS

Skryshevsky et al., "Impedance spectroscopy of single graphene layer at gas adsorption," Phys. Status Solidi A, vol. 212, No. 9, pp. 1941-1945 (Apr. 2015).
Wang et al., "A Review on Graphene-Based Gas/Vapor Sensors with Unique Properties and Potential Applications," Nano-Micro Lett. Jul. 2015, 8(2): pp. 95-119.

\* cited by examiner

FIG. 3
(Prior Art)

RESONANT GAS SENSOR

RELATED APPLICATIONS

The present application is a continuation-in-part of and claims the benefit of priority to U.S. patent application Ser. No. 16/706,542 titled "Resonant Gas Sensor", filed on Dec. 6, 2019, which claims the benefit of priority to U.S. Prov. Pat. App. Ser. No. 62/815,927 titled "Resonant Gas Sensor", filed on Mar. 8, 2019, and which is a continuation of, and claims the benefit of priority to U.S. patent application Ser. No. 16/239,423 (now U.S. Pat. No. 10,502,705) titled "Resonant Gas Sensor", filed on Jan. 3, 2019, which claims the benefit of priority to U.S. Prov. Patent Application Ser. No. 62/613,716 titled "Volatiles Sensor", filed on Jan. 4, 2018, all of which are hereby incorporated by reference in their entirety.

TECHNICAL FIELD

This disclosure generally relates to a sensor system for detecting an analyte (including chemical and biological hazards), and more particularly to the detection of the analyte using a resonant circuit defined by carbon-based sensing material that produces an electrical signal characteristic of the analyte in response to stimulus by a signal.

DESCRIPTION OF RELATED ART

Sensors include devices, modules, machines, or subsystems that detect events or changes in its surrounding environment to send detected information to other electronics, frequently a computer processor. With advances in micromachinery and easy-to-use microcontroller platforms, the uses of sensors have expanded beyond traditional fields of temperature and pressure detection or flow measurement. Application areas include manufacturing and machinery, airplanes and aerospace, cars, medicine, robotics, and many other aspects of our day-to-day life. To address such widespread and potentially dissimilar needs, a wide range of sensors have been developed, including those directed to measuring chemical and physical properties of materials, including materials of particular interest, such as controlled substances or harmful pathogens. Graphene, a two-dimensional material made of carbon atoms that demonstrates outstanding properties, and sensors are seen by many as a natural combination, given graphene's large surface-to-volume ratio, unique optical properties, excellent electrical conductivity, high carrier mobility and density, high thermal conductivity and many other attributes can be greatly beneficial for many traditional sensor functions and goals. The relatively large surface area of graphene is able to enhance surface loading of desired biomolecules, and excellent conductivity and small band gap can also be beneficial for conducting electrons between various biomolecules and the electrode surface. FIG. 1 shows a plan view of such a conventional graphene-based sensor prepared for sensing one or more chemical vapors or gases, illustrated as a system 100. A sensing material 120 acts as a chemiresistor (referring to a material that changes its electrical resistance in response to changes in a nearby chemical environment) and bridges two electrodes 110 and 111. When vapors pass through and interact with the sensing material 120, a change in resistance of the graphene sensing material can be observed for a resistance measurement 160 to be accordingly taken.

FIG. 2 is a perspective view of a conventional graphene-based sensor 200 configured as a field effect transistor (FET), described as a type of transistor which uses an electric field to control the flow of current. A first metal electrode 210 acts as a source, a second metal electrode 211 acts as a drain. The graphene-based sensor 200 also includes a gate 220. The electrodes 210, 211 and the channel 220 are mounted on a dielectric material 230. Operation of the sensor 200 results in the identification of specific analyte species and quantifications of the concentration levels of the species in the analyte. FIG. 3 provides a table listing examples of conventional gas sensors, including graphene-based materials including epitaxial-G, G-ozone treated, G-exfoliated, G-nanomesh, rGO, G-microfiber and graphene sheets can be used to make chemiresistors, FETs, optical sensors, and conductivity sensors. Such sensors, however, typically do not have sufficient sensitivity in ppb levels and lack the high selectivity needed in conventional real-world settings involving multiple sources of interferences. Conventional systems also can rely on adding energy, such harnessing energy available from heat, to drive sensing reactions within the sensor to improve sensing sensitivity. And, equipment required for conventional gas sensors cannot be easily miniaturized, which limits their use in mobile applications. It would be desirable to detect an analyte (such as a chemical or biological hazard) on a flexible substrate, such as a parcel or package flap, powered by modern energy harnessing functionality.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter. Moreover, the systems, methods, and devices of this disclosure each have several innovative aspects, no single one of which is solely responsible for the desirable attributes disclosed herein.

One innovative aspect of the subject matter described in this disclosure can be implemented as a sensor configured to detect an analyte. The sensor can include an antenna disposed on a substrate. A sensing material is also disposed on the substrate and is electrically coupled to the antenna. The sensing material can include a carbon structure including a multi-modal distribution of pore sizes that define a surface area including bonding sites configured to interact with one or more additives and the analyte. The carbon structure is configured to generate a resonant signal indicative of one or more characteristics of the analyte in response to an electromagnetic signal. The carbon structure can include a plurality of distinctly sized interconnected channels defined by the surface area and configured to be infiltrated by the analyte, and a plurality of exposed surfaces configured to adsorb the analyte. Each of the one or more distinctly sized interconnected channels can include at least one of microporous pathways or mesoporous pathways. Each of the microporous pathways or mesoporous pathways can be configured to increase a responsiveness of the sensing material proportionate to an amount of the analyte within the carbon structure.

In some implementations, the sensing material is integrated into the antenna or positioned within a vicinity of the antenna. One or more characteristics of the resonant signal can be indicative of a presence of one or more known harmful substances in the sensing material. The indication can be based on a comparison of the one or more characteristics of the resonant signal with one or more characteristics of the known harmful substances.

In some implementations, the sensing material is configured to oscillate at: a first amplitude at one or more resonant frequencies of the sensing material; and a second amplitude at one or more non-resonant frequencies of the sensing material, wherein the first amplitude is greater in magnitude than the second amplitude.

In some implementations, a pair of electrodes can be electrically coupled to a dielectric and the sensing material. The sensing material and the dielectric can be positioned between the pair of electrodes and comprise a tank circuit.

In some implementations, the carbon structure is at least partially bound by a polymer, which can include one or more polymer additives configured to alter electrical properties of the sensing material by interacting with the analyte. The carbon structure can include one or more tuned materials configured to increase a resonance sensitivity of the sensing material across one or more frequency ranges. The carbon structure further can include a plurality of three-dimensionally (3D) structured aggregates. Each aggregate of the plurality of 3D structured aggregates can include a plurality of nanoparticles.

In some implementations, the 3D structured agglomerates are configured to generate an impedance response indicative of one or more characteristics of the sensing material based on an excitation signal. The sensing material can be configured to generate one or more resonant signals indicative of a type of the analyte based on an electromagnetic signal.

Another innovative aspect of the subject matter described in this disclosure can be implemented as a sensor system for detecting an analyte. The sensor system can include a substrate, and a resonant circuit configured to be removed without requiring replacement of the substrate. The resonant circuit can be disposed on the substrate can include an antenna disposed on the substrate. A sensing material is disposed on the substrate and is electrically coupled to the antenna. The sensing material can include a carbon structure with a multi-modal distribution of pore sizes that define a surface area including bonding sites for interaction with one or more additives and the analyte. The carbon structure can generate a resonant signal indicative of one or more characteristics of the analyte in response to an electromagnetic signal. The carbon structure can include a plurality of distinctly sized interconnected channels defined by the surface area and configured to be infiltrated by the analyte, and a plurality of exposed surfaces configured to adsorb the analyte.

In some implementations, the analyte can be configured to be at least partially contained within a package. The resonant circuit can be attached to the antenna by compression. Degradation of a removable top layer of the sensing material can be indicative of a need for replacement of the removable top layer.

In some implementations, the resonant circuit can be configured to detect the analyte flowing from a vehicle. The resonant circuit can include a capacitive element that at least partially contains the sensing material.

In some implementations, the sensor system can include a pair of electrodes electrically coupled to the capacitive element, and a circuit configured to generate the electromagnetic signal.

In some implementations, a frequency of a peak in the resonant signal induced by dithering the electromagnetic signal can be indicative of a presence of the analyte in the sensing material. The sensor system can include a circuit configured to determine a presence of the analyte in the sensing material based on a comparison between the frequency of the peak in the resonant signal and one or more frequencies indicative of harmful substances.

Another innovative aspect of the subject matter described in this disclosure can be implemented as a method for detecting an analyte in a sensing material defined by a carbon structure including a plurality of distinctly sized interconnected channels. The method can include receiving the analyte through the one or more distinctly sized interconnected channels into the carbon structure, receiving at least one electromagnetic signal configured to oscillate over a range of frequencies, and identifying the analyte based on a resonant signal of the carbon structure responsive to the at least one electromagnetic signal.

A frequency of a peak in the resonant signal induced by dithering the at least one electromagnetic signal can be indicative of a presence of the analyte in the sensing material.

Details of one or more implementations of the subject matter described in this disclosure are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Implementations of the subject matter disclosed herein are illustrated by way of example and are not intended to be limited by the figures of the accompanying drawings. Like numbers reference like elements throughout the drawings and specification. Note that the relative dimensions of the following figures may not be drawn to scale.

Figure 3:
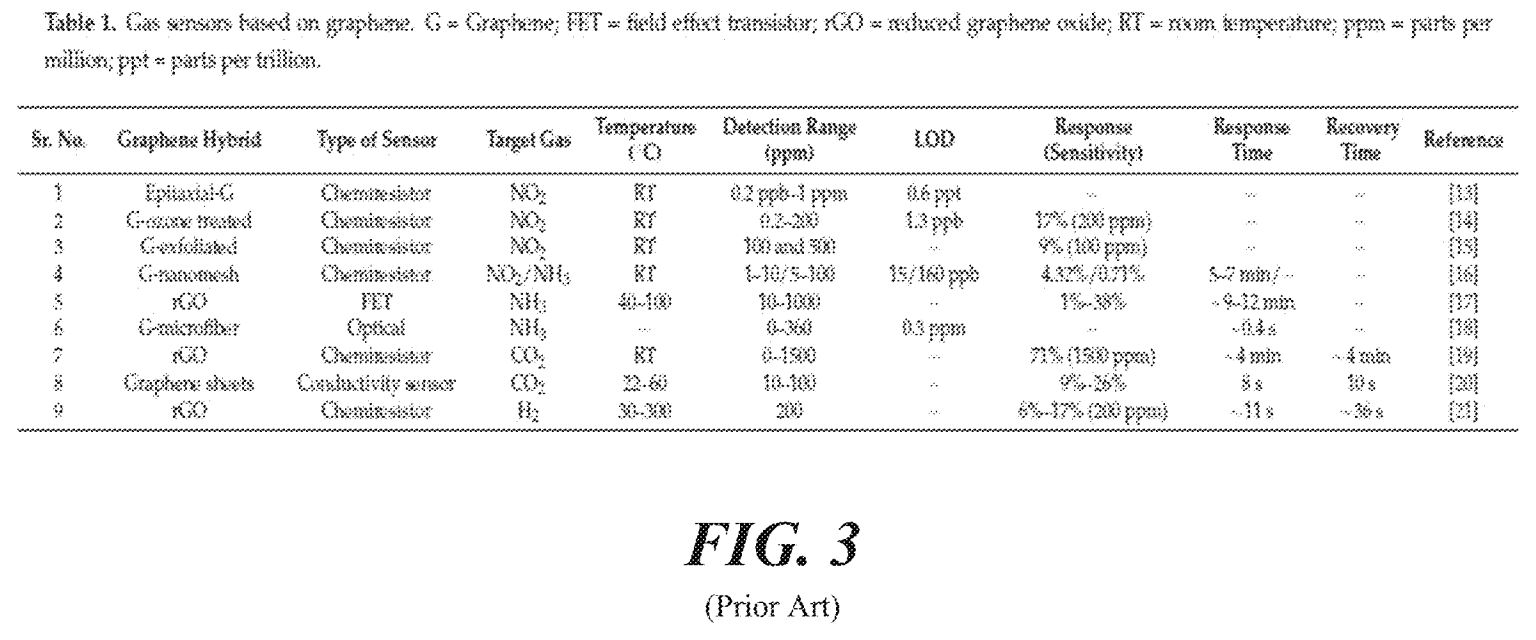

FIG. 3 (Prior Art) is a table listing examples of conventional gas sensors based on graphene.

DETAILED DESCRIPTION

Introduction

Figure 1:
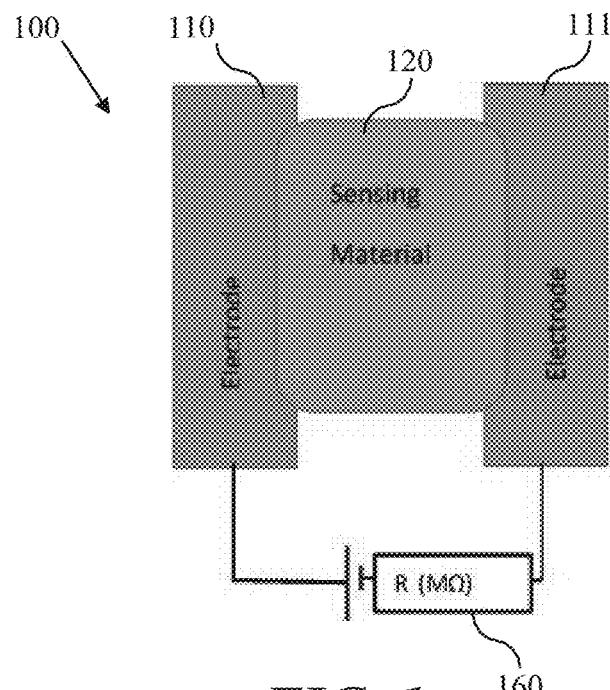
FIG. 1 (Prior Art) is a plan view of a conventional graphene-based sensor for chemical vapor or gas sensing.
Figure 2:
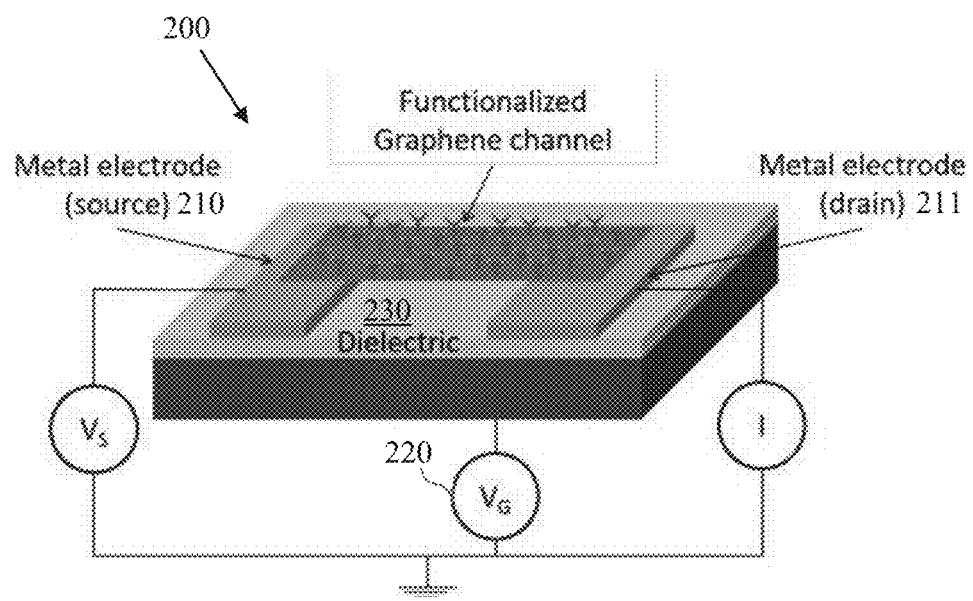
FIG. 2 (Prior Art) is a perspective view of a conventional graphene-based sensor 200 configured as a field effect transistor (FET).

Various implementations of the subject matter disclosed herein relate generally to systems and methods of using a sensor to detect an analyte, such as a controlled substance by incorporating sensing materials including unique carbon-based structures. Reactive chemical additives can be incorporated into the sensing material where, upon exposure to an analyte intended for detection, the reactive chemical additive can chemically react with the analyte to correspondingly alter the electrical properties of the sensing material and thereby enhance its ability to accurately identify and detect a quantity of the analyte. The electrical properties of the sensing material can be interrogated by an electromagnetic signal or otherwise engaged with by circuitry in, or associated with, the sensor, where the change in electrical properties due to analyte exposure can be detected pursuant to detection of a unique response to a ping-stimulus, such as a sweeping or targeted signal or pattern of signals. The presently disclosed sensing materials can include various carbons and structures that are coupled with the sensor to accordingly improve sensitivity and power consumption while accurately detecting an analyte. Such disclosed carbon structures incorporated in sensing materials provide compatibility with miniature gas sensors, enabling many end-use application areas otherwise not available to fixed fluid, including gaseous phase substances, analyte sensors.

Example end-use application areas of the presently disclosed systems and methods include environmental monitoring of indoor air quality, water testing, waste water treatment, chemical manufacturing, and total ion counts, industrial safety, such as toxic compound detection, food and beverage industry applications, such as monitoring of food fermentation process, freshness/ripeness and spoilage, first response applications, such as chemical agents, and explosive materials, and biomedical applications, such as infection monitoring, antioxidant level monitoring, and biospecimen monitoring. Analytes, such as volatile liquids, gases or vapors, can be sensed by the presently disclosed sensing materials using impedance spectroscopy, such as measuring the dielectric properties of a medium as a function of frequency based on the interaction of an external field with the electric dipole moment of sample, also expressed by permittivity, techniques and so-equipped sensors. Disclosed materials use relatively low cost formative materials and methods for printing of electrical components on backing materials, such as labels, smart cards, and packaging materials, which can be integrated with other hardware components on a substrate, such as a flexible substrate, to create versatile electro-active sensing devices and systems.

Sensors for detecting chemicals, including controlled substances, such as cocaine or fentanyl, in a vapor, such as including particulate matter suspended in air, phase can be made using 3D graphene-inclusive materials, where such carbons can be tailored to sense a specific chemical targeted for detection by the sensing materials. Printed sensor systems can be configured as flexible labels that can be affixed to packages, parcels, or containers such as shipping boxes to monitor and indicate suspicious contents within the container. More than one sensor can be printed on a single label, where each sensor can be configured to detect a different chemical such that a combination of the chemicals detected by the different sensors on the label can indicate the presence of a compound that is unstable or otherwise difficult to detect. Disclosed systems include those with a resonant circuit with a transducer, where the resonant circuit is disposed on a substrate, such as a flexible surface including a parcel flap. The resonant circuit includes a sensing material defined by a carbon-based structure with a plurality of porous pathways. Any one or more of the plurality of pathways can be configured to engage in an interaction with a fluid analyte to transduce a characteristic electrical signal unique thereto based on the interaction. The sensing material is disposed on the substrate and electrically coupled to the transducer. Usage of unique carbon-inclusive materials and composites produced by novel microwave plasma and thermal cracking equipment enable activation of the presently disclosed sensor systems to function by using relatively low power, such as that made available by energy harvesting technologies.

Carbon Materials for Gas Sensors

The present gas sensors for detecting analytes, such as volatile compounds, can incorporate unique carbon materials, such as produced using microwave plasma or thermal cracking equipment, as described further below.

3-dimensionally structured, such as microporous, mesoporous, and/or hierarchical structures, carbon, such as graphene. particles are used in gas sensors. The porosity, surface area, and surface philicity/polarity of the carbon particles can be tuned to change the properties of the particles, such as their complex impedance. The carbon acts as an electrically conductive scaffold supporting a second phase of material, such as a dielectric polymer, such that the properties of the combined particle, such as the electrical resistivity and/or the complex impedance, can change when exposed to one or more analytes. The properties of the carbon and the second phase of material can each be tuned to produce a combined material that is electrically conducting, molecular sieving, and an efficient gas adsorption framework, and is capable of detecting a wide range of analytes, such as volatile gases or vapors, for numerous applications. The particulate carbon described herein is used to form frequency selective materials, which can be used in resonant circuits within the present gas sensors.

The carbon particles are formed into a film using a polymer as a binder. In some cases, the surface area and porosity of the carbon particles, and the polymeric binder to carbon particle ratio can be tuned to provide molecular sieving, such as effecting rate of analyte, such as volatile organic compound, diffusion, or mass transport, and separation, for enhanced molecular size and shape selectivity.

The carbon, such as graphene, surfaces can be modified, such as functionalized to affect adsorption behavior and the dielectric properties of the material. Such surface modification of the sensing material can increase the dielectric changes, from both the graphene and polymer materials, upon interaction with an analyte and therefore improve the sensitivity and analyte selectivity of the sensor.

The carbon surface can be functionalized to tune the philicity/polar nature of the surface and as a result, a sensing material can be created with an engineered response to humidity. For example, sensors can be fabricated with non-wetting hydrophobic graphene surfaces to minimize effect of moisture/humidity.

Alternatively, sensors with a 2-element sensor array containing hydrophilic and hydrophobic specific graphene detectors, such as multiples of each type of sensor in an array configuration, can provide greater sensitivity and selectivity by accounting for, such as subtracting out, background effects from humidity. This approach can be extended to arrays of sensors with differently tuned sensing materials to enable various materials, such as impurities, to be accounted for through signal processing methods, such as high/low response of a 2-level, or higher order, detector array.

The unique carbon material is a particulate carbon with improved properties compared to conventional carbon materials. For example, the particulate carbon can have high compositional purity, high electrical conductivity, and a high surface area compared to conventional carbon materials. The high surface area, for example, provides a large concentration of gas sensing sites, such as bonding sites for reactive chemical additives used to detect target chemical species, which improves the lower detection limit of the sensor. Additionally, the high electrical conductivity is beneficial to gas sensors because less power is lost due to parasitic resistive heating of the electrical components of the gas sensors, such as the electrodes, or the sensing material of the gas sensors.

The particulate carbon also has a structure that is beneficial for gas sensor performance, such as small pore sizes and/or a mesoporous structure. In some cases, a mesoporous structure can be characterized by a structure with a wide distribution of pore sizes, such as with a multimodal distribution of pore sizes. For example, a multimodal distribution of pore sizes can be indicative of structures with high surface areas and a large quantity of small pores that are efficiently connected to a substrate supporting the material and/or current collector via material in the structure with larger feature sizes, such as that provide more conductive pathways through the structure.

Some non-limiting examples of such structures are fractal structures, dendritic structures, branching structures, and aggregate structures with different sized interconnected channels, such as composed of pores and/or particles that are roughly cylindrical and/or spherical. A mesoporous structure can be particularly beneficial to gas sensors. Not to be limited by theory, the mesoporous structure can provide pathways for a rapid mass transport of the analyte within the carbon matrix, while microporosity simultaneously provide high surface area structures beneficial to the detection limit.

The particulate carbon materials used in the gas sensors described herein are produced using microwave plasma reactors and methods, such as any appropriate microwave reactor and/or method described in U.S. Pat. No. 9,812,295, entitled "Microwave Chemical Processing," or in U.S. Pat. No. 9,767,992, entitled "Microwave Chemical Processing Reactor," which are assigned to the same assignee as the present application, and are incorporated herein by reference as if fully set forth herein for all purposes.

The gas sensors described herein contains one or more particulate carbon materials. The particulate carbon materials used in the gas sensors described herein described herein are described in U.S. Pat. No. 9,997,334, entitled "Seedless Particles with Carbon Allotropes," which is assigned to the same assignee as the present application, and is incorporated herein by reference as if fully set forth herein for all purposes. The particulate carbon materials contain graphene-based carbon materials that comprise a plurality of carbon aggregates, each carbon aggregate having a plurality of carbon nanoparticles, each carbon nanoparticle including graphene, optionally including multi-walled spherical fullerenes, and optionally with no seed particles, such as with no nucleation particle. In some cases, the particulate carbon materials are also produced without using a catalyst. The graphene in the graphene-based carbon material has up to 15 layers. A ratio, such as percentage, of carbon to other elements, except hydrogen, in the carbon aggregates is greater than 99%. A median size of the carbon aggregates is from 1 micron to 50 microns, or from 0.1 microns to 50 microns. A surface area of the carbon aggregates is at least 10 $m^2/g$, or is at least 50 $m^2/g$, or is from 10 $m^2/g$ to 300 $m^2/g$, or is from 50 $m^2/g$ to 300 $m^2/g$, when measured using a Brunauer-Emmett-Teller (BET) method with nitrogen as the adsorbate. The carbon aggregates, when compressed, have an electrical conductivity greater than 500 S/m, or greater than 5,000 S/m, or from 500 S/m to 20,000 S/m.

The particulate carbon materials used in the gas sensors described herein are described in U.S. Pat. No. 9,862,606 entitled "Carbon Allotropes," which is assigned to the same assignee as the present application, and is incorporated herein by reference as if fully set forth herein for all purposes. The particulate carbon materials contain carbon nanoparticles comprising at least two connected multi-walled spherical fullerenes, and layers of graphene coating the connected multi-walled spherical fullerenes. Additionally, the carbon allotropes within the carbon nanoparticles can be well ordered. For example, a Raman spectrum of the carbon nanoparticle using 532 nm incident light can have a first Raman peak at approximately 1350 cm−1 and a second Raman peak at approximately 1580 cm−1, and a ratio of an intensity of the first Raman peak to an intensity of the second Raman peak is from 0.9 to 1.1. In some cases, the atomic ratio of graphene to multi-walled spherical fullerenes is from 10% to 80% within the carbon nanoparticles.

The particulate carbon materials described herein are produced using thermal cracking apparatuses and methods, such as any appropriate thermal apparatus and/or method described in U.S. Patent Application Ser. No. 9/862,602, entitled "Cracking of a Process Gas," which is assigned to the same assignee as the present application, and is incorporated herein by reference as if fully set forth herein for all purposes.

The particulate carbon used in the present gas sensors contains more than one type of carbon allotrope. For example, the particulate carbon can contain graphene, spherical fullerenes, carbon nanotubes, amorphous carbon, and/or other carbon allotropes. Some of these carbon allotropes are further described in the related U.S. Patents and Patent Applications mentioned in this disclosure.

Additionally, the different carbon allotropes in the particulate carbon can have different morphologies, such as mixtures of low and high aspect ratios, low and high surface areas, and/or mesoporous and non-mesoporous structures. The use of particulate carbon with combinations of different allotropes, and in some cases different morphologies, can enhance the electrical and mechanical properties of different components of the present gas sensors, such as electrodes or sensing materials. The mass ratio of a first carbon allotrope, such as with high electrical conductivity and/or a mesoporous structure, to a second carbon allotrope, such as a long chain carbon allotrope, in the particulate carbon can be from 70:30 to 99:1, or from 80:20 to 90:10, or from 85:15 to 95:5, or is about 85:15, or is about 90:10, or is about 95:5. For example, mesoporous carbon allotropes in the particulate carbon can provide high surface area and/or high electrical conductivity, and the addition of long chain, such as high aspect ratio, carbon allotropes in the particulate carbon can improve the mechanical strength, adhesion and/or durability of the present gas sensor components.

The particulate carbon used in the present gas sensors contains particles containing graphene, such as with one or more of the properties described herein, and particles containing long chain carbon allotropes such as spherical fullerenes connected in a string-like arrangement, or carbon nanotube bundles. The long chain carbon allotropes have aspect ratios greater than 10:1, or from 10:1 to 100:1, or about 10:1, or about 20:1, or about 50:1, or about 100:1. The long chain carbon allotropes have dimensions from 50 nm to 200 nm wide by up to 10 microns in length, or from 10 nm to 200 nm wide by from 2 microns to 10 microns in length. Additional particles containing long chain carbon allotropes are described in the related U.S. Patents and Patent Applications mentioned in this disclosure. The mass ratio of a graphene-containing carbon allotrope to a long chain carbon allotrope in the particulate carbon can be about 85:15, or about 90:10, or about 95:5. The long chain carbon allotropes can interlock with other conductive, and in some cases structured, or mesoporous, carbon allotropes in the particulate carbon and can form an interlocked hybrid composite allotrope gas sensor component, such as electrode or sensing material, with improved mechanical properties compared to components without long chain carbon allotropes. The addition of long chain, such as fibrous like, carbon increases the medium range, such as 1 micron to 10 microns conductivity, and the distribution of the other carbon allotrope, such as prevents agglomeration of the other carbon allotrope, such as mesoporous graphene particles, while improving mechanical stability. Furthermore, the addition of long chain carbon allotropes can provide additional porosity around the carbon chain, which increases ion conductivity and mobility in the gas sensor component. These long chain fibers can enable reduced calendering pressure during fabrication, leading to components with increased local voidage or porosity, while maintaining the same, or better, mechanical stability, such as tolerance to delamination and/or cracking, as components without long chain carbons that are calendared at higher pressures. Reduced calendering pressure can be advantageous because the higher porosity achieved using a lower pressure leads to increase ion conductivity and/or mobility. Additionally, the addition of long chain carbon, such as fibers, can improve the elongation/strain tolerance over conventional slurry cast components. In some cases, the elongation/strain tolerance, such as the maximum strain to failure, or the amount of performance degradation for a given strain, can be increased by as much as 50% over conventional slurry cast components. The addition of long chain carbon allotropes to the particulate carbon in a gas sensor component enables the use of less binder, or the elimination of the binder, in the component.

In a non-limiting example, a mechanically robust, hybrid composite electrode or sensing material film can contain particulate carbon with a combination of lower density, such as mesoporous, hierarchical graphene-containing particles, such as with particle sizes from 15 to 40 microns in diameter, and higher density particles containing long chains of connected spherical fullerenes, such as with sizes 50 to 200 nm wide by up to 10 microns in length. The mass ratio of graphene carbon allotropes to the long chain allotropes in this example is about 85:15. The particulate carbon in this example has high electrical conductivity, due to the high electrical conductivity of the graphene and/or spherical fullerenes, and the long chain allotropes provide mechanical reinforcement.

In conventional films, or patterned traces, containing conductive and/or active materials particles, a binder is often used to improve the mechanical properties. The present gas sensor components are mechanically reinforced by long chain carbon allotropes, which enables the reduction or the elimination of a binder in the components. For example, an interlocked hybrid composite allotrope film, or patterned trace, containing mesoporous graphene and long chain carbon allotropes can be formed with suitable mechanical properties without the use of a binder. Such components with no binder can also be free-standing components, such as are mechanically stable without being attached to a substrate.

An interlocked hybrid composite allotrope gas sensor component can be formed by sintering the particulate carbon after component formation, such as after printing, or slurry casting. This process can be used to consolidate and strengthen the composite component structure.

Carbon particles and aggregates containing graphite and graphene were generated using a microwave plasma reactor system, described in U.S. Pat. No. 9,767,992, entitled "Microwave Chemical Processing Reactor." The microwave plasma reactor in this example had a main body made from stainless steel with a quartz inner wall material. However, the quartz inner wall material is not needed in all cases, and similar carbon materials can be produced in reactors without quartz in or adjacent to the reaction zone. It is beneficial to produce the particulate carbon in a reactor that does not have quartz in or adjacent to the reaction zone, because materials, such as oxygen, can decompose out of the quartz and become incorporated as unwanted impurities in the produced carbon materials. The reaction zone volume was approximately 45 cm$^3$. The precursor material was methane and was optionally mixed with a supply gas (such as argon). The flow rate of methane was from 1 to 20 L/min, the flow rate of the supply gas was from 0 to 70 L/min. With those flow rates and the tool geometry, the residence time of the gas in the reaction chamber was from approximately 0.001 second to approximately 2.0 seconds, and the carbon particle production rate was from approximately 0.1 g/hr to approximately 15 g/hr. After the aggregates were synthesized and collected, they were post-processed by annealing at a temperature from 1,000 to 2,200° C. in an inert atmosphere for a duration of approximately 60 to approximately 600 minutes.

The particles produced in this example contained carbon aggregates containing a plurality of carbon nanoparticles, where each carbon nanoparticle contained graphite and graphene and did not contain seed particles. The particles in this example had a ratio of carbon to other elements (other than hydrogen) of approximately 99.97% or greater.

Figure 4:
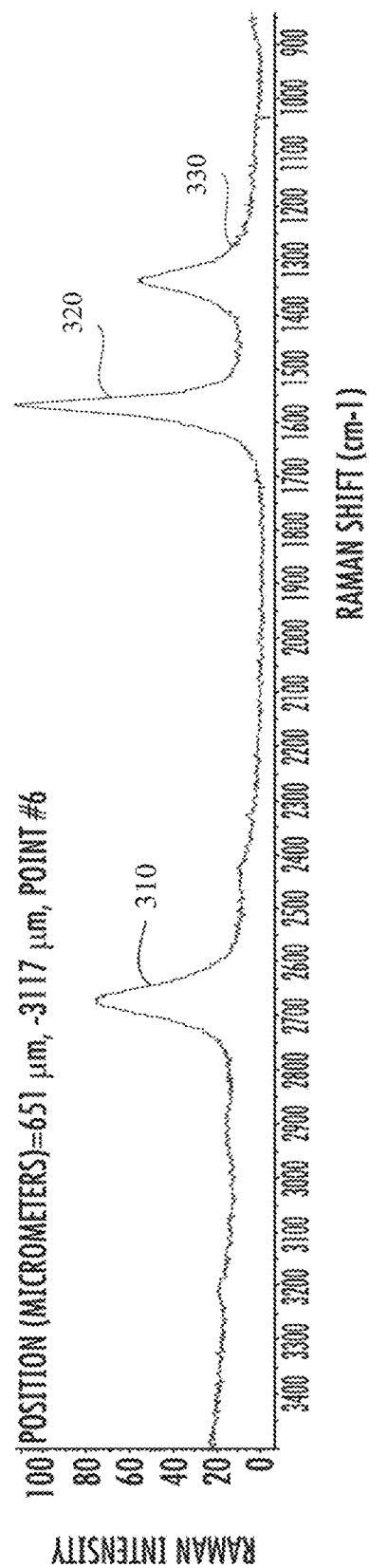
FIG. 4 shows a Raman spectrum from particulate carbon containing graphene, in accordance with some implementations.

FIG. 4 shows a Raman spectrum of the particulate carbon of this example, taken using 532 nm incident light. The particles in FIG. 4 were produced using precursors containing argon. The spectrum has a 2D-mode peak 310 at approximately 2690 cm$^{-1}$, a G-mode peak 320 at approximately 1580 cm–1, and a D-mode peak 330 at approximately 1350 cm–1, and the 2D/G intensity ratio is greater than 0.5. The 2D/G intensity ratio for the particles produced in FIG. 4 is approximately 0.7.

The size of the aggregates in this example have a median of approximately 11.2 microns as synthesized, and approximately 11.6 microns after annealing. The size distribution of the as-synthesized aggregates had a 10th percentile of approximately 2.7 microns, and a 90th percentile of approximately 18.3 microns. The annealed aggregates size distribution had a 10th percentile of approximately 4.2 microns, and a 90th percentile of approximately 25.5 microns.

The electrical conductivity of the aggregates was measured after being compressed into pellets. The as synthesized, such as before annealing, material had a conductivity of 800 S/m when compressed using 2,000 psi of pressure, and a conductivity of 1,200 S/m when compressed using 12,000 psi of pressure. The annealed material had a conductivity of 1,600 S/m when compressed using 2000 psi of pressure, and a conductivity of 3,600 S/m when compressed using 12,000 psi of pressure.

Figure 5A:
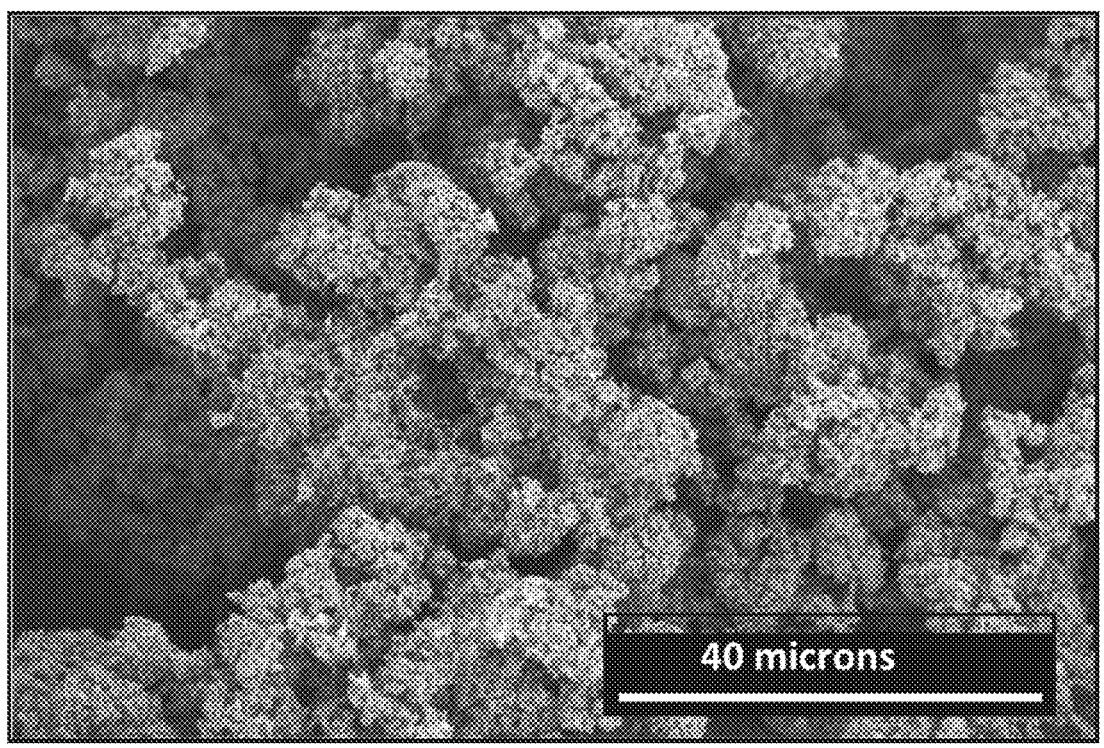
FIGS. 5A and 5B show scanning electron microscope (SEM) images from particulate carbon containing graphene, in accordance with some implementations.
Figure 5B:
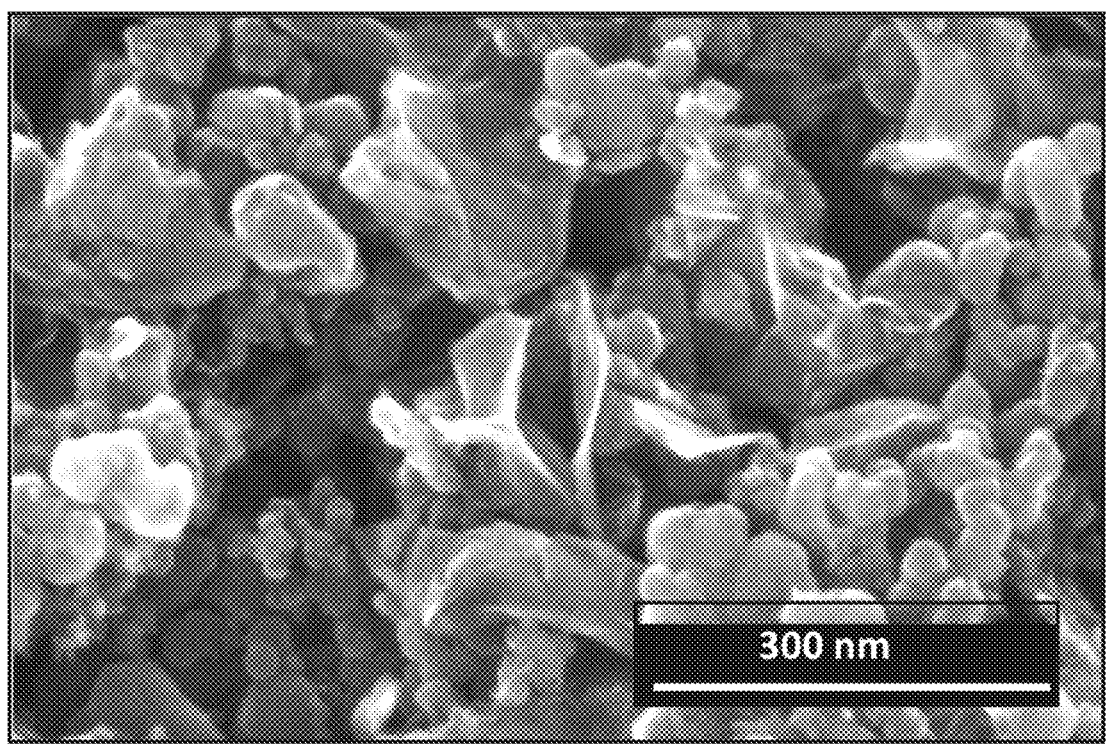
Figure 6A:
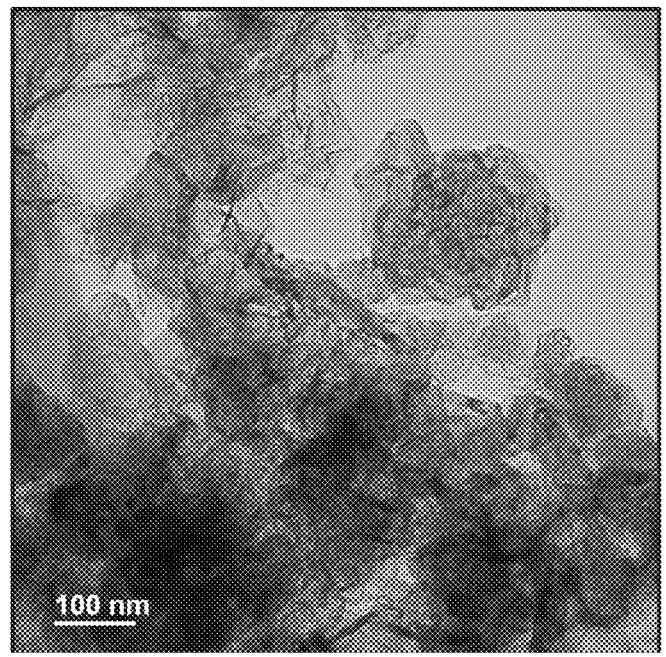
FIGS. 6A and 6B show transmission electron microscope (TEM) images from particulate carbon containing graphene, in accordance with some implementations.
Figure 6B:
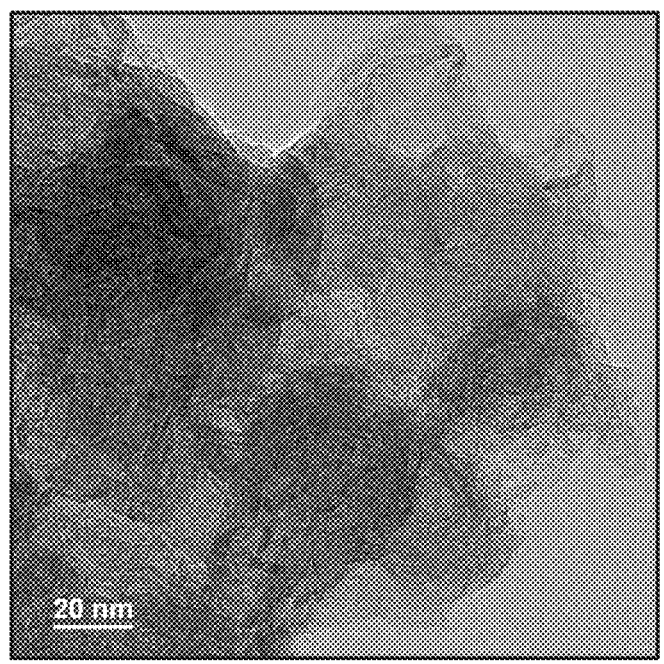

FIGS. 5A and 5B show SEM images, and FIGS. 6A and 6B show TEM images, of the carbon aggregates of the particulate carbon of this example showing graphite and graphene allotropes. The layered graphene is clearly shown within the distortion, wrinkles, of the carbon. The 3D structure of the carbon allotropes is also visible. The carbon allotropes in this example have a 3D structure with a hierarchical mesoporous, few layer, graphene structure with a specific edge-to-basal plane ratio. The edge-to-basal plane ratio for the graphene in the present particulate carbon is about 1:10, or about 1:100, or from 1:10 to 1:100.

The surface area of the aggregates in this example were measured using the nitrogen BET method and the density functional theory (DFT) method. The surface area of the aggregates as determined by the BET method was approximately 85.9 m$^2$/g. The surface area of the aggregates as determined by the DFT method was approximately 93.5 m$^2$/g.

In contrast to conventionally produced carbon materials, the microwave plasma reactor produced carbon particles and aggregates in this example contained graphite and graphene had high purity, high electrical conductivities, and large surface areas. Additionally, these particles had Raman signatures indicating a high degree of order and contained no seed particles.

The particulate carbon in the present gas sensors contains doped carbon materials (such as carbon doped with H, O, N, S, Li, Cl, F, Si, Se, Sb, Sn, Ga, As, and/or other metals), undoped carbon materials, or combinations thereof. Doped carbon can also include carbon with a matrix allotrope doped with carbon atoms, not in the matrix structure, and/or doped with other types of carbon allotropes. Doped carbon materials can also be doped with functional groups, such as amine (NH$_3$) groups. Doped carbon materials are formed using a dopant material, where the dopant material is introduced within a gas, liquid, or colloidal dispersion and fed into a reactor that is used to produce the doped particulate carbon. For example, dopant materials can be combined with a hydrocarbon precursor material and cracked in a reactor, such as a microwave plasma reactor or a thermal reactor, to produce a doped particulate carbon.

The particulate carbon in the present gas sensors contains nano-mixed particulate carbon. The surface area, structure, and/or surface activity of the present particulate carbon materials are tuned by nano-mixing the carbon particles within the carbon materials with particles of other materials. Particles of nano-mix additive materials can be beneficially integrated with particles of the graphene-based carbon on a particle level, which shall be referred to as nano-mixing in this disclosure. The average diameter of the particles of the nano-mix additive material and the graphene-based carbon materials in the nano-mixed particulate carbon can be from 1 nm to 1 micron, or from 1 nm to 500 nm, or from 1 nm to 100 nm, or can be as small as 0.1 nm. The nano-mix additive material and the graphene-based carbon material are chemically bound, or are physically bound, together in the nano-mixed particulate carbon. The nano-mixing involves introducing nano-mix additives during particulate formation, such as during a hydrocarbon cracking process in a microwave plasma reactor or in a thermal reactor, such that the nano-mix additive material is integrated into the graphene-based carbon material as the carbon material is produced, rather than combining a carbon raw material with an additive in a later process as in certain conventional methods. The nano-mix additive material can be introduced as a gas, liquid, or colloidal dispersion into a reactor that is used to produce the nano-mixed particulate carbon. As an example, silicon can be input into a reactor along with a hydrocarbon process gas, or other carbon-containing process material such as a liquid alcohol, to produce silicon nano-mixed with graphene, graphene-based carbon materials, and/or other carbon allotropes. In other examples, the resulting nano-mixed particulate carbon can contain particles of O, S, Li$_x$S$_y$, where x=0-2 and y=1-8, Si, Li$_{22}$Si$_5$, Li$_{22}$-xSi$_5$-y, where x=0-21.9, and y=1-4.9, and Li$_{22-x}$Si$_{5-y-z}$M$_z$, where x=0-21.9, y=1-4.9, z=1-4.9, and M is S, Se, Sb, Sn, Ga, or As, and/or other metals.

The particulate carbon to be used in the present gas sensors are produced and collected, and no post-processing is done. The particulate carbon can be produced and collected, and some post-processing is done. Some examples of post-processing include mechanical processing, such as ball milling, grinding, attrition milling, micro-fluidizing, jet milling, and other techniques to reduce the particle size without damaging the carbon allotropes contained within. Some examples of post-processing include exfoliation processes such as shear mixing, chemical etching, oxidizing, such as through the Hummer method, thermal annealing, doping by adding elements during annealing, such as O, S, Li, Si, Se, Sb, Sn, Ga, As, and/or other metals, steaming, filtering, and lyophilizing, among others. Some examples of post-processing include sintering processes such as SPS, Spark Plasma Sintering, such as Direct Current Sintering, Microwave, and ultraviolet (UV), which can be conducted at high pressure and temperature in an inert gas. Multiple post-processing methods can be used together or in series. The post-processing can produce the functionalized carbon nanoparticles or aggregates described herein.

The particulate carbon described herein can be combined with a second phase of material to create composite films. These composite films can be fabricated utilizing different methods to create specific detector responses.

In an example, solid carbon particles, such as particle size from 0.3 microns to 40 microns, and polymer beads, such as ball mixed for size reduction and improved aggregation, can be mixed in a ratio of 90:10 respectively, or in ratios from 95:10 to 5:95. This mixture can then be cast onto a substrate, such as one containing pre-fabricated electrodes, or an antenna platform, and then treated, such as using a low temperature, post treatment in an inert gas oven, a reactive gas oven, or a vacuum oven.

In another example, the mixing of the solid carbon particles and polymer beads described in the example above can be further combined with a solvent to form an ink, which can then be deposited onto a substrate, such as cast using doctor blade, or printed. After deposition, the film can then be treated at a low temperature to remove the solvent and consolidate the film.

In another example, particulate carbon can be encapsulated with a polymer to form colloidal core-shell structures that can be printed onto antenna platform using various techniques including inkjet printing, aerosol spray coating, spin coating and roll coating.

In another example, the particulate carbon can be combined with a soluble polymer to form jet-table inks for printing. In such applications, conductive binders, such as silver flakes/particles, can also be added to tune the dielectric properties, such as at particle-particle contact points.

Figure 7:
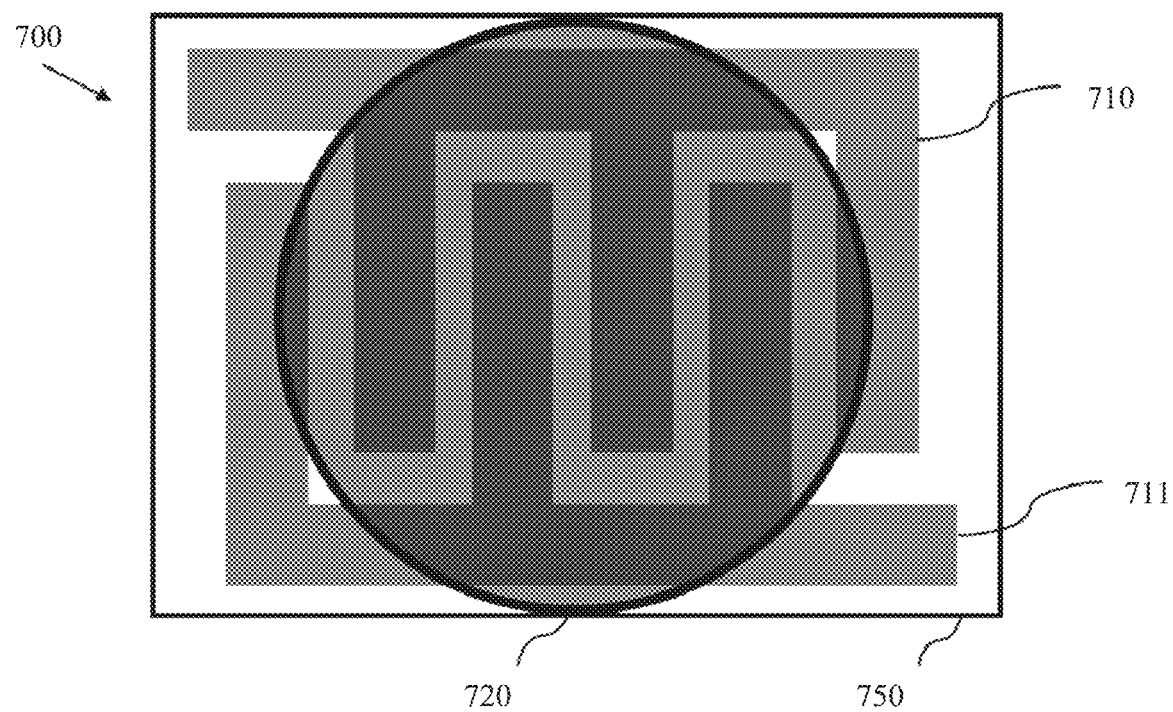
FIG. 7 shows an example of a sensor component where a first electrode and a second electrode are configured as interdigitated fingers, in accordance with some implementations.

FIG. 7 shows an example of an electrochemical gas sensor 700 in another embodiment of an electrochemical sensor, where a first electrode 710 and a second electrode 711 are configured as interdigitated fingers to increase the area for electrical interaction between the electrodes, which can be beneficial for example in cases where the electrolyte contains the sensing material, such as reactive chemical additives. Additionally, such an interdigitated electrode geometry can be used to tune the capacitance of the sensor element to allow it to be integrated with other circuit elements more advantageously. The first and second electrodes 710 and 711 can be printed using carbon-based conductive inks, optionally containing one or more redox mediators. An electrolyte 720, which can include a redox mediator, can be printed as a layer over the electrodes 710 and 711. The electrolyte 720 can be configured as a circular layer, such as by applying a droplet of the electrolyte during fabrication of the sensor. However, the electrolyte 720 can be formed, such as by being inkjet printed or cast, in other geometries, such as a rectangular layer, or other patterned shape to impact the electrical properties of the sensor circuit. Some non-limiting examples of materials for the electrolyte are polymers, such as poly (ether urethane) (PEUT), polyepichlorohydrin (PECH), polyisobutylene (PIB), and alkyl cellulose), ceramics, or monomers that solidify into a suitable solid electrolyte. The first electrode 710, second electrode 711, and electrolyte 720 can all be printed on a flexible or rigid substrate 750, where the substrate 750 may be, for example, an $SiO_2$-coated paper or polymeric material.

The electrodes and electrolytes of the present embodiments contain the particulate carbon described herein and are tuned to sense the target chemical. In some embodiments, tuning the particulate carbon materials includes functionalizing the particulate carbon to be sensitive to certain materials. For example, the particulate carbon can contain one or more reactive chemistry additives which react with a target chemical to be detected. Some non-limiting examples of target chemicals moieties that can be detected by the sensors of the present disclosure include, but are not limited to, acetone, ammonia, carbon monoxide, ethanol, hydrogen peroxide ($H_2O_2$), nitro ($NO_2$) groups, oxygen, and water, such as to detect humidity levels. Characteristic interactions between these chemicals and reactive chemistry additives of one or more of the gas sensor components are used to detect the presence of these chemicals. For example, $NO_2$ groups withdraw electrons, $NH_3$ gas is an electron donor, $CO_2$ gas is an electron donor, acetone is a neutral molecule, $H_2O_2$ is an oxidizer, and ethanol is an electron donor. When a gas species interacts with a reactive chemistry additive in the sensing material, these types of interactions change the electrical properties (e.g., the conductivity, or the complex impedance) of the sensing material, which causes a change in the measured response from the gas sensor indicating the presence of the species.

In an example, a sensing material in a gas sensor contains particulate carbon containing p-type doped graphene semiconductors, which have a response towards $NO_2$, $CO_2$, or $NH_3$ gases. $NO_2$ gas or $NO_2$ containing molecules adsorb/desorb on a graphene surface via three possible adsorption configurations: nitro, nitrite, and cycloadditions. During these configurations, there is a charge transfer between $NO_2$ molecules and the p-type graphene molecules. The electron withdrawing effect of $NO_2$ increases the hole-density which leads to a decrease in resistance, or a change in the complex impedance spectrum. $CO_2$ and $NH_3$ are donors, so the resistance of the p-type doped graphene semiconductors increases (or the complex impedance spectrum changes) due to a depletion in hole density.

In another example, a sensing material in a gas sensor contains particulate carbon containing n-type graphene composites, which can be used for acetone sensing. In graphene-zinc-ferrite composites, surface oxygen sp hybrid orbitals interact with acetone to form $CO_2$ and $H_2O$ and release free electrons which decreases the resistance (or change the complex impedance) of the sensing material. In a further example, a graphene composite with iron (II) reacts with $H_2O_2$ to produce $O_2$ and Fe (III). Either $O_2$ can be detected, or UV can be used to check the wavelength of the Fe (III) complex.

In some embodiments, the carbon allotropes within the particulate carbon in the present sensors can be tuned to detect the desired chemical by utilizing a certain microstructure, such as the porosity or curvature, such as curved graphene, of the carbon. The carbons can contain $sp^3$, $sp^2$ and/or sp hybrid orbitals, or a combination of these. In other embodiments, tuning can be achieved by adding reactive chemistry additives in the form of functional groups to the carbon, such as oxygen, ketones, or carboxyl. The tuning in the various embodiments may be achieved during initial production of the carbon, and/or by post-processing after the carbon has been made. The post-processing, as described herein, can include steps such as changing the surface area of the carbon material, such as by ball milling, changing the conductivity, adding functional groups, or a combination of these.

In an experimental run, a sensor was used to test for the presence of hydrogen peroxide. The interdigitated fingers in this example contained the particulate carbon described herein. The redox mediator solution was 10 μL of 5 mM bis(pentamethylcyclopentadienyl) iron (II), 100 mM tetraethylammonium tetrafluoroborate, and 25 mM KOH in butylmethylimidazolium tetrafluoroborate. The sensor was activated by applying a voltage of 1.0 V in the absence of peroxide and then allowed to equilibrate for 5 minutes to establish a baseline current. The sensor was then put into an atmosphere containing peroxide, single digit parts per million to parts per billion, for 1.0 hr, after which a 1.0 V voltage was applied, and the current was measured. The results are shown in Table 1 below.

TABLE 1

Sample experimental results for electrochemical sensor

|  | No peroxide | Peroxide vapor present | |
| --- | --- | --- | --- |
|  |  | Test cycle 1 | Test cycle 2 |
| Current | 2.63 µA | 19.7 µA | 20.5 µA |
| E we | 311 nWh | 1912 nWh | 1973 nWh |

As can be seen from Table 1, the baseline currents increased approximately 650%—from 2.63 µA to 19.7 µA—and remained constant (20.5 µA) for the second hold/test cycle. Thus, the electrochemical sensor demonstrated the ability to detect peroxide with high sensitivity using low amounts of electrical power.

High Frequency Sensors

Some electrochemical sensors utilize direct current (DC) electrical signals to detect changes to a sensing material, such as changes in charge carrier concentration causing a change in resistance to indicate chemistry, and/or changes in molecular structure causing a change in capacitance to indicate chemistry. While such DC gas sensors are capable of sensing low levels of chemistry, the detection range without costly equipment, such as utilizing high power energy sources, to drive chemical reactions makes widespread adoption impractical for most applications. Alternating current (AC) signals can be used to detect characteristic, reversible impedance responses of a sensing material. In some such gas sensors, a multi-frequency AC signal, such as RF current with a range of frequencies, is applied to a sensing material within a sensing circuit and the complex impedance of the circuit is detected. The frequencies of the AC signals used in such "high frequency" gas sensors are typically greater than 1 kHz, or are from 1 kHz to 20 GHz, or are from 100 kHz to 20 GHz.

High frequency gas sensors contain AC circuits with a sensing material incorporated. The geometries and materials in the AC circuits can be tuned to be sensitive to certain frequency ranges, and the complex impedance of the AC circuit changes upon interaction with an analyte that changes the complex impedance of the sensing material. In general, the complex impedance of a material within the AC circuit will affect the signals detected from the circuit and can be tuned to tune the response of the circuit. For example, the sensing material can contain a carbon material, the properties of the carbon material can affect the complex impedance, and therefore the complex impedance of a carbon sensing material and a sensing circuit containing that material can be controlled by specifically tuning the properties of the carbon materials, such as the structure of the carbon materials, the types of allotropes present, and the concentration of defects in any ordered carbon allotropes present.

High frequency gas sensors contain a structured material within the sensing material. The complex impedance of a structured material is a result of the inherent materials properties forming the structure as well as the geometry of the structure, such as the pore size, the pore spacing and the macroscopic shape of the material. In the case of composite structured materials, the distribution of the materials with different properties also affects the complex impedance of the material. For example, electrically conductive materials, such as the particulate carbons described herein, can be structured into a mesoporous structure, and be decorated with other materials such as dielectrics or permeable materials. The structure, composition, distribution of materials, and/or the concentration of impurities and/or defects are changed to tune the complex impedance of a structured sensing material within a high frequency gas sensor. Such a structured sensing material is beneficial in high frequency resonant gas sensors because they contain a variety of random paths and path lengths available for conduction at many frequencies, which can provide a sensor with a wide bandwidth of possible frequencies with which to detect a target analyte. The structured materials, such as with the particulate carbon described herein, are frequency selective materials, which are used in high frequency circuits within the present gas sensors.

Dielectric polarization modification impedance spectroscopy is utilized, which is a low-cost method for detecting low concentrations of analytes, such as volatile gases or vapors, in a gas sensor. An impedance spectroscopy measurement can be used to detect the modulation of properties of a sensing material containing reactive chemical additives, such as a structured sensing material containing particulate carbon and a redox mediator in the presence or absence of an analyte. For example, selective frequency interrogations of S21, such as the transmission of a high frequency signal through an AC circuit or system, and S11, such as the reflectance of a high frequency signal from an AC circuit or system, can be used to detect a change in the complex impedance of the sensing material and/or circuit, or system, as a whole.

The operation of the gas sensor relies on a change in the measured S21 or S11 value upon exposure to an analyte.

The combination of such high frequency gas sensors, such as utilizing impedance spectroscopy, and the unique properties of the particulate carbon described herein, such as structure, surface area, and conductivity, enables gas sensors that are able to generate the same results as the more costly counterparts, such as detecting an analyte with concentrations in the parts per million (ppm) or parts per billion (ppb) ranges, at a greatly reduced price, and an improved ease of adoption and portability. The low power requirement of the disclosed examples allow for the system to be powered by battery systems and in some cases using energy harvester systems. Additionally, the imaginary part of the complex impedance of the sensing materials described herein have spectral signatures, such as peaks in the spectra, that can discriminate one molecular arrangement from others, enabling the detection of several molecules with one sensor.

Figure 8:
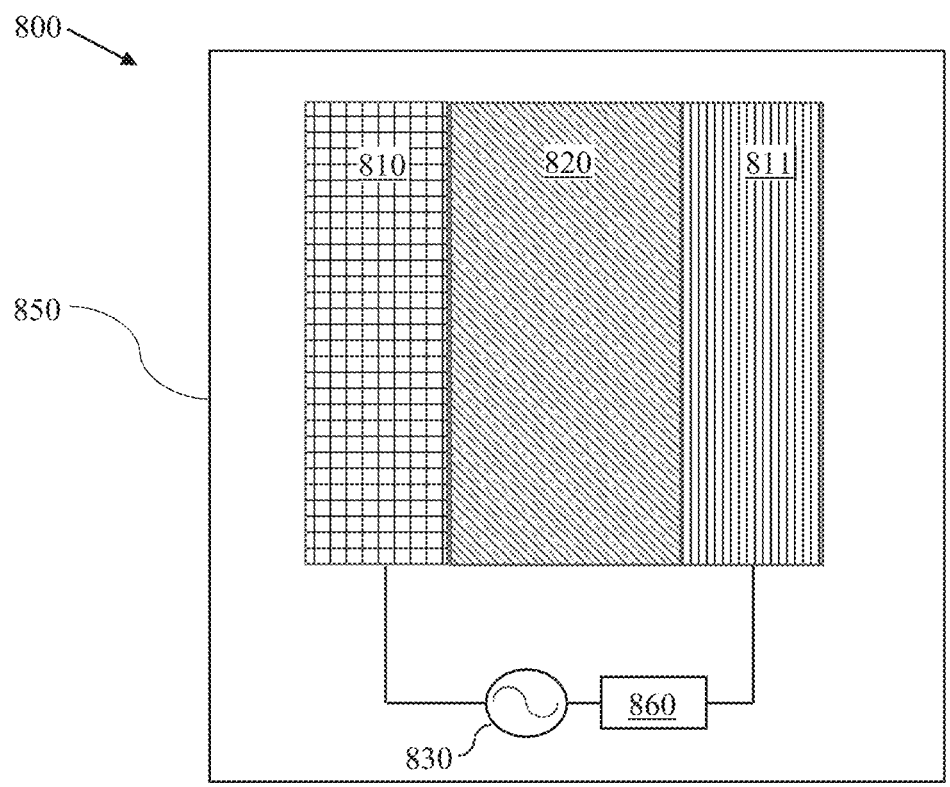
FIG. 8 shows an example of a chemical sensor in which high frequency spectroscopy is used as the detection method, in accordance with some implementations.

FIG. 8 shows an example of a chemical sensor 800 in which high frequency, such as impedance, spectroscopy is used as the detection method. Sensor 800 includes a first electrode 810, a second electrode 811, and a dielectric 820 sandwiched between the electrodes 810 and 811, all of which are arranged on substrate 850. The electrodes 810 and 811 and/or the dielectric 820 are printed from inks on the substrate 850. Substrate 850 may be rigid or flexible, for example, a label. In some cases, a device may be formed on both sides of a substrate. The electrodes 810 and 811 contain the particulate carbon described herein, silver particles, metal particles, conductive oxide particles, such as indium tin oxide and/or fluorine-doped tin oxide particles, or other conductive particulate materials, including any aspect ratio particulates, such as those shaped as spheroids, rods, and wires. One or both of the electrodes 810 and 811 can contain a carbon allotrope such as, but not limited to, graphene, graphene oxide, carbon nano-onions, and/or carbon nanotubes. One electrode includes a metal while the other electrode does not. One or both electrodes 810 and 811 and/or dielectric 820 can include a reactive chemistry additive, such as a redox mediator, as described in reference to the electrochemical sensors above, which is tuned to one or more target analyte, such as volatile gas or vapor, species.

In operation, an AC source 830 applies AC signals having a range of frequencies such as greater than 1 kHz, or from 10 kHz to 20 GHz, or from 10 kHz to 1 GHz, or from 500 kHz to 20 GHz, or from 500 MHz to 20 GHz to the sensor 800, and a detection circuit 860 detects a change in impedance at specified frequencies when the target substance interacts with, such as is absorbed into, or adsorbed onto, the sensing material. The sensor 800 uses an impedance spectroscopy technique, in which specific target analyte chemicals interact with the sensing material, such as containing the particulate carbon described herein, causing a change in the complex impedance of the sensing material. The change in the complex impedance can then be measured by the detection circuit 860, and the measured change used for detecting the target substance. The sensing material contains tailored carbon and a reactive chemistry additive with electrons that interact with the target compound and change the resonance frequency.

High Frequency Resonant Sensors

One type of a high frequency gas sensor is a resonant gas sensor. A resonant gas sensor contains one or more sensing materials, and changes to the resistivity and permittivity of the sensing materials result in changes to the resonant behavior of the sensor. Such a resonant gas sensor can be printed and utilize small electronics, such as a small IC chip, such that it can be miniaturized and produced at low cost. Such low-cost miniature resonant gas sensors have a myriad of applications including product labels on food packaging, shipping labels on packages, and portable hazardous and/or toxic gas sensors. Low cost resonant gas sensors are enabled by the particulate carbon materials described herein, which improve the resonant gas sensor sensitivity allowing for low power signals to produce adequate responses. For example, the high the surface area and mesoporous structure of the particulate carbon allows more analyte vapors to enter into the structure and increases the changes in the sensing material resistivity and permittivity for a given analyte concentration. The sensing materials or materials making up the other elements, such as with the particulate carbon described herein, contain frequency selective materials, which are used to tune the resonant frequencies of the resonant circuits within the present gas sensors.

The resonant gas sensors contain pickup electrodes to provide AC signal power input to the sensing materials and detect an output from the sensing materials. The geometries of the constituent elements can be tuned in order to produce a resonant structure with certain frequency response in the sensor. In addition, the materials properties, such as resistivity and/or complex permittivity, of the sensing material can also be tuned to form a resonator structure or composite with a certain spectral frequency response. Tuning the materials properties and resonant structure geometries can be advantageous to enhance the performance of the gas sensor to be more sensitive in certain frequency ranges.

A resonant gas sensor system includes a microprocessor, which provides a signal to a transducer, such as an antenna, that drives a sensing material in the resonant gas sensor over a specific frequency range. The microprocessor can also detect the response, such as the complex impedance spectrum of the sensor. In different cases, the response can be a reflected AC signal, such as S11, or a transmitted AC signal. The sensing material can be integrated into the transducer or be a separate element. Different resonant gas sensor architectures are described below. In some cases, the response is compared to a database, such as a library, of resonance spectra for a variety of molecular chemistries related to certain molecules of interest, such as those in explosives, or rotting foods. The functionality of the detector and transducer are integrated into a single, monolithic, patterned film structure, optionally integrated with other electronics such as an integrated microprocessor and/or communication chip, such as to communicate a detection event to another device. The microprocessor, and other optional integrated electronics, can be powered using an integrated battery or using energy harvesting structures, such as using an antenna that absorbs RF energy or a photocell that absorbs light, coupled to an integrated capacitor to store the harvested energy. In some cases, such an integrated sensor can contain a resonant structure with engineered properties, such as conductivity, and geometry, to minimize the antenna absorption loss at high frequency.

A resonant gas sensor contains a set of electrically conductive elements that form a resonant structure. The resonant structure itself exhibits resonance or resonant behavior, that is, it naturally oscillates at some frequencies, called its resonant frequencies, with greater amplitude than at others. These resonant structures within the sensors are used to select specific frequencies from a signal, such as the signal provided by the microprocessor in the resonant gas sensor systems described herein. For example, a resonant gas sensor can contain two conductive electrodes surrounding and/or electrically coupled to a dielectric or an electrically conductive gas sensing material, all of which form a single resonant structure, along with other components of the system, in some cases. In another example, a transducer, such as an antenna, can be excited with a signal, and the sensing material can be arranged adjacent to the transducer such that the complex impedance of the sensing material impacts a detected response. In some cases, the electrode(s) and/or the gas sensing material can contain the particulate carbon described herein. In some cases, the electrode(s) and/or the gas sensing material can be printed and/or be deposited from a liquid, gas, or ink dispersion.

In some cases, the resonant structures described above can be incorporated into the resonant gas sensor circuit to form an LC tank circuit. For example, a coiled antenna can be used as an inductive element, and a sensing material between two electrodes can be used as a capacitive element, and the inductive and capacitive elements can be connected in parallel or in series to form a tank circuit in a resonant gas sensor. A single transducer structure, such as a coiled antenna, can contain, or be formed from, the sensing material, and also provide the inductive and capacitive elements of the tank circuit. Such multi-functional transducers can be driven by a microprocessor, and upon interaction with an analyte the transducer material properties change, which change the characteristic response of the gas sensor circuit, which in turn can be measured by detection circuitry to detect the presence of an analyte. In other cases, the transducer does not contain sensing materials, and the sensing materials change the properties of one or more elements within the tank circuit, such as the capacitance of a capacitive element, which change the characteristic response of the circuit, which in turn can be measured by detection circuitry to detect the presence of an analyte.

When a gas sensitive material interacts with an analyte, the complex electrical materials properties of the permittivity $\epsilon = \epsilon' - j\epsilon''$, where j is the imaginary unit, and permeability $\mu = \mu' - j\mu''$ change. In a resonant gas sensor, the varying material properties can lead to a change in the wave propagation of a signal, such as a multi-frequency signal provided by a microprocessor, through a resonant structure, such as an LC tank circuit, an antenna, or a microstrip line. In addition to the materials properties, the wave propagation of a signal in a resonant gas sensor also depends on the geometry of the structures formed by the elements of the sensor. In some cases, the resonant structures in the resonant gas sensor contain one or more waveguides, and the wave propagation of a signal also depends on the design of the waveguide(s). Generally, electromagnetic waves are guided to a desired transmission mode by restricting their expansion in one or two dimensions. One transmission structure for waves with a transversal electromagnetic mode (TEM) is the planar microstrip line, consisting of a strip conductor and a ground plane either separated by a dielectric substrate or separated by a dielectric material on a single side of a substrate. The two-dimensional structure of microstrips make them well suited for miniaturization and integration with other components and, because of the planar structure, they can be fabricated conventionally by thick or thin film technology.

In some cases, the circuit elements, such as resonant structures, are formed, such as by printing, on one side of a substrate to create a resonator, such as a microstrip line with co-planar electrodes separated by a dielectric gap. In addition, or in the alternative, the elements are formed, such as by printing, on both sides of a substrate to create a resonator, such as a patch antenna separated from a ground plane electrode by a dielectric substrate containing a sensing material. The substrate can be many different materials including rigid or flexible materials, those with suitable dielectric properties, a polymer sheet, or paper. In some cases, a base layer can be pre-deposited on the substrate to act as an anchoring layer to absorb part of the deposited, such as printed, material and or to create a barrier to prevent absorption of the deposited material into the substrate, such as paper.

Figure 9A:
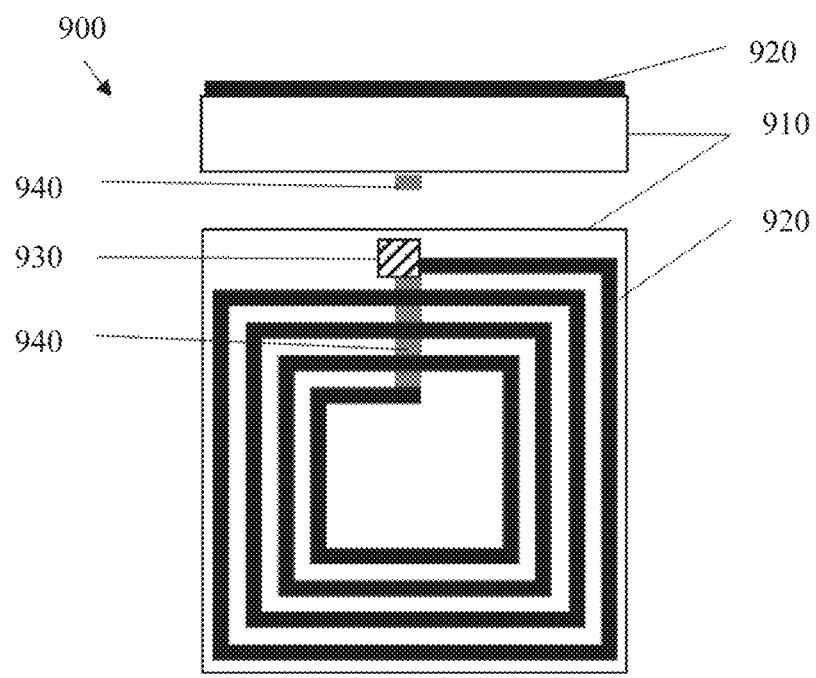
FIG. 9A shows a non-limiting example of a resonant gas sensor in side view and plan view, in accordance with some implementations.

FIG. 9A shows a non-limiting example of a resonant gas sensor 900 inside view and plan view, including a substrate 910, a transducer 920 (that may be alternatively referred to or otherwise include a spiral transducer, or an antenna), a microprocessor 930, and a ground electrode 940. A first terminal of the microprocessor 930 is electrically coupled to a first terminal of the transducer 920, and the ground electrode 940 completes the circuit from a second terminal of the transducer to a second terminal of the microprocessor 930. In this example, the ground electrode is connected to the second terminal of the transducer 920 and to the second terminal of the microprocessor 930 through vias in the substrate, not shown. The transducer 920 in this example is a spiral with successive loops with different dimensions. The microprocessor 930 provides AC signals at different frequencies to the first terminal of the transducer 920 and measures the response, either reflected from the transducer 920 or transmitted through the transducer 920. In this example, the transducer 920 contains a sensing material, such as a redox mediator, which is sensitive to an analyte, such that when the resonant gas sensor 900 is exposed to the analyte, the complex impedance of the transducer 920 changes, and the response detected at the microprocessor 930 changes indicating the detection of the analyte. In other words, the complex permittivity and/or permeability of the sensing material changes upon exposure to an analyte, which changes the resonant frequency of the sensor circuit indicating the detection of the analyte.

Figure 9B:
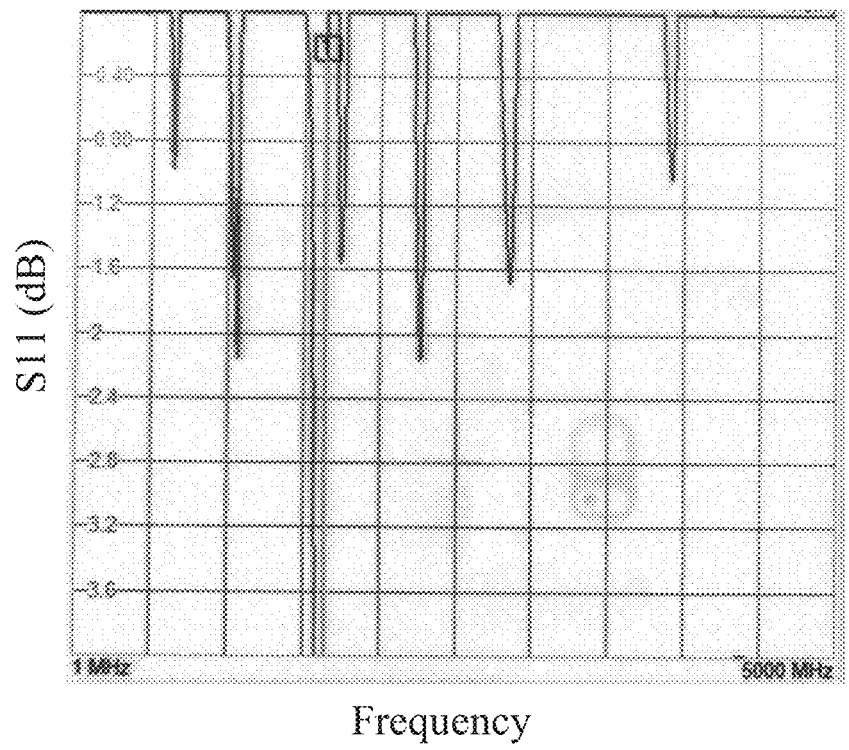
FIG. 9B shows an example of a response from a resonant gas sensor in the presence of an analyte of interest, in accordance with some implementations.

FIG. 9B shows an example of a response from a resonant gas sensor, such as 900 in FIG. 9A in the presence of an analyte of interest. The x-axis in the plot in FIG. 9B is frequency, from 1 MHz to 5000 MHz, and the y-axis is the reflected signal from the transducer, such as the transducer 920 in FIG. 9A, such as S11, which is the signal reflected back from the first terminal of the transducer in dB. The troughs in the plot in FIG. 9B indicate the resonant frequencies of the circuit, where the AC signals are not reflected, such as dissipated, in the resonant circuit. These troughs can change depending on the type and concentration of an analyte present, and in some cases can be compared to a library to determine the identity of a detected analyte species. Since the location of the troughs depends on the resonant frequencies of the entire gas sensor circuit, a library of analyte species and concentrations is created for a specific resonant gas sensor design and materials set.

Figure 9C:
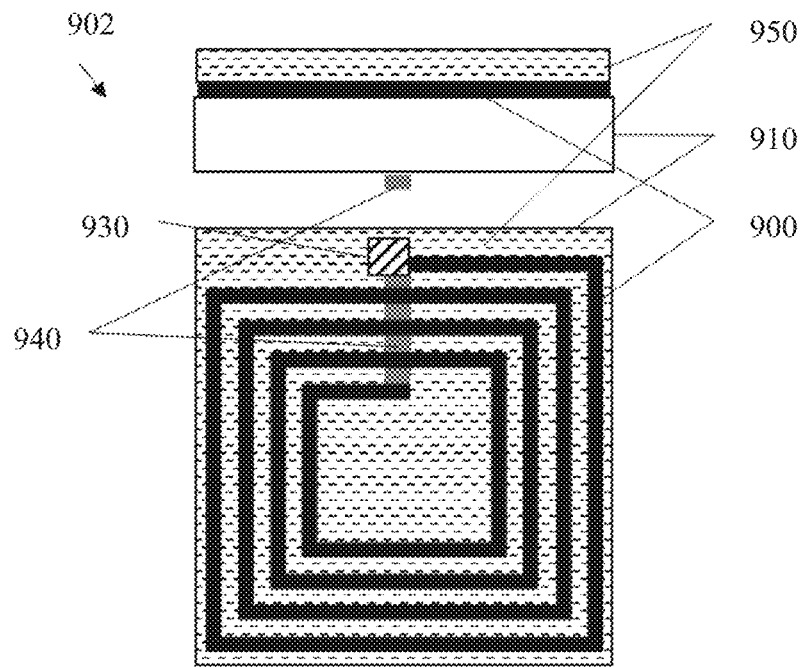
FIGS. 9C and 9D show non-limiting examples of resonant gas sensors in side view and plan view, in accordance with some implementations.

FIG. 9C shows a non-limiting example of a resonant gas sensor 902 inside view and plan view, including a substrate 910, a transducer 920, a microprocessor 930, a ground electrode 940, and a sensing material 950. The resonant gas sensor 902 is like the resonant gas sensor 900, and further includes a sensing material 950 disposed above and in between successive loops of the transducer 920. In this example, the sensing material is sensitive to an analyte, such that when the resonant gas sensor 902 is exposed to the analyte, the frequency response of the resonant circuit formed by the transducer 920 and sensing material 950 changes, and the response detected at the microprocessor 930 changes indicating the detection of the analyte. The change in frequency response in this example can be caused by a change in the inductance of the transducer 920 and/or a change in the capacitance between successive loops of the transducer 920, which change the resonant frequencies of a tank circuit formed by the transducer 920 and sensing material 950. In other words, the complex permittivity and/or permeability of the sensing material changes upon exposure to an analyte, which changes the resonant frequency of the sensor tank circuit indicating the detection of the analyte.

Figure 9D:
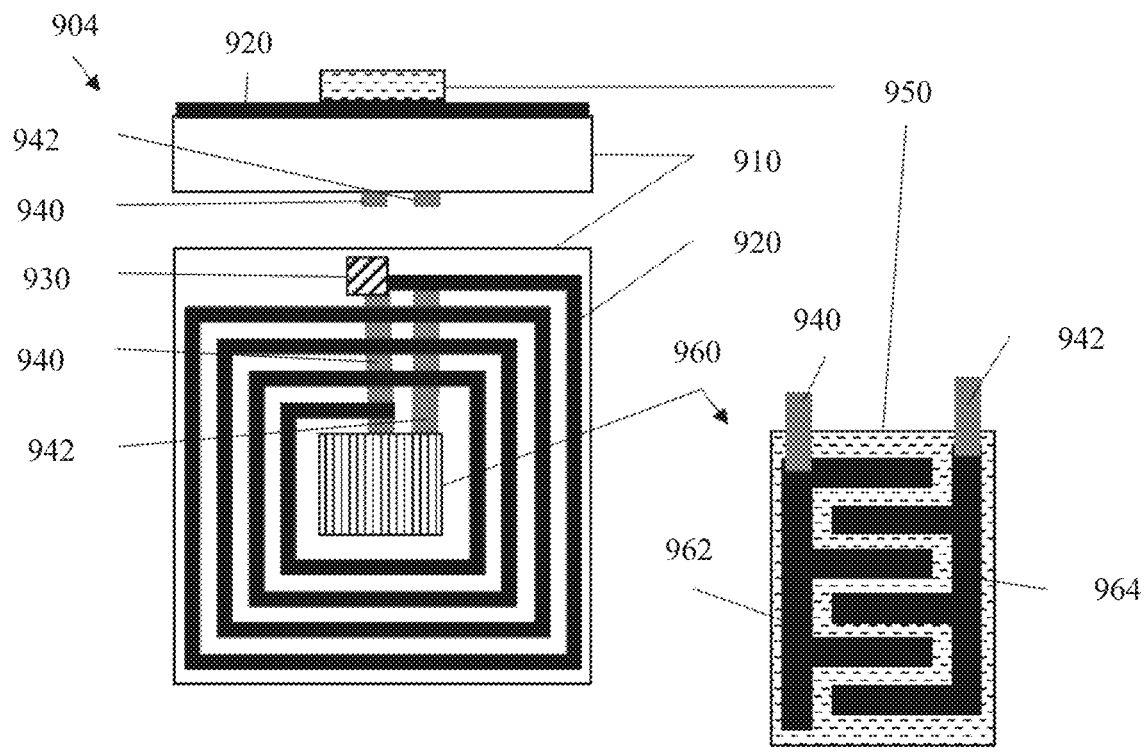

FIG. 9D shows a non-limiting example of a resonant gas sensor 904 in side view and plan view, including a substrate 910, a transducer 920, a microprocessor 930, a ground electrode 940, a second electrical connection 942, a sensing material 950, and a capacitive element 960. The resonant gas sensor 904 is similar to the resonant gas sensor 900, and further includes a capacitive element 960. The capacitive element 960 in this example is formed from interdigitated electrodes 962 and 964. In this example, the capacitive element 960 has the sensing material 950 disposed on and between the interdigitated fingers 962 and 964. In this example, the capacitive element 960 is wired in parallel with the transducer 920; the ground electrode 940 is electrically coupled to electrode 962 of the capacitive element 960, and the second electrical connection 942 couples the electrode 964 of the capacitive element 960 to the first terminal of the transducer 920, as described in resonant gas sensor 900 in FIG. 9A. Therefore, an LC tank circuit, with the inductive element and capacitive element in parallel, is formed from the transducer 920 and the capacitive element 960 in this example. In this example, the sensing material 950 (which can include or otherwise be formed as a composite detecting film), such as a redox mediator, is sensitive to an analyte, such that when the resonant gas sensor 904 is exposed to the analyte, the capacitance of the capacitive element 960 changes, and the response detected at the microprocessor 930 changes indicating the detection of the analyte. In other words, the complex permittivity and/or permeability of the sensing material changes upon exposure to an analyte, which changes capacitance of the capacitive element 960 and the resonant frequency of the sensor tank circuit indicating the detection of the analyte. One advantage of separate inductive and capacitive elements, such as shown in resonant gas sensor 904 is that the resonant frequency of the tank circuit can be tuned. One example of this is lowering the resonant frequency to a lower frequency range, such as from about 20 GHz to about 1 GHz, to reduce the cost of the electronics required to drive the sensor circuit.

Figure 9E:
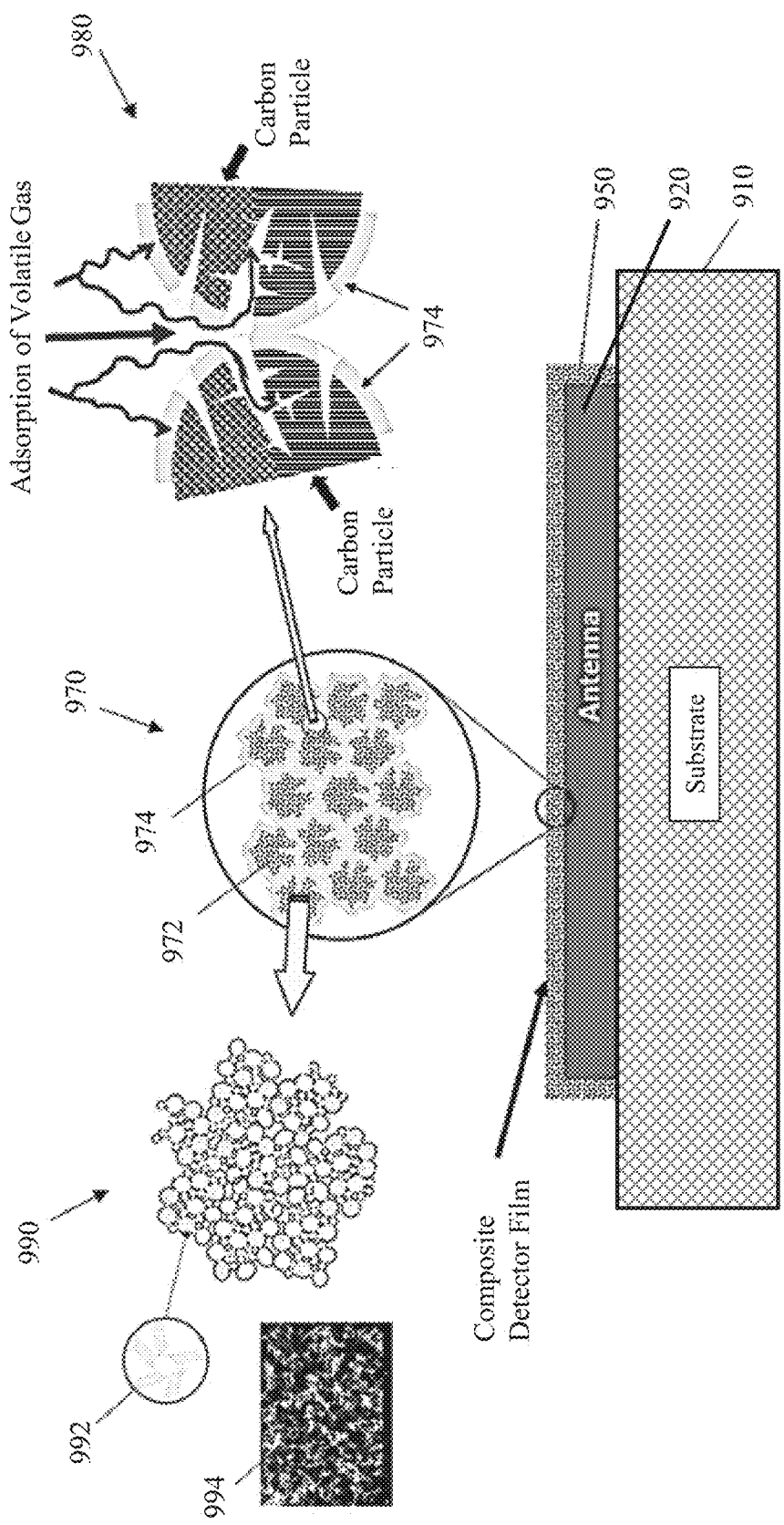
FIG. 9E shows a non-limiting example of a resonant gas sensor with a sensing material containing particulate carbon, in accordance with some implementations.

FIG. 9E shows a non-limiting example of a resonant gas sensor containing a substrate 910, a transducer antenna 920, and a sensing material 950 for sorption of an analyte, such as volatile organic solvent vapors. The sensing material 950 contains a structured particulate conducting phase encapsulated with a polymeric binder. Insets 970 and 980 show schematics of the particulate conducting phase 972 encapsulated by the polymeric binder 974. Inset 980 shows a volatile gas, or more generally, an analyte, adsorbed by the polymeric binder and/or the interior surfaces of the particulate carbon. The polymeric binder contains one or more reactive chemical additives, which interact with an analyte and cause the electrical properties of the sensing material 950 to change. A reactive chemistry additive, such as a dissolved salt, can be deposited on and within the pores of the particulate carbon. In some cases, the reactive chemical additives can be incorporated into the particulate carbon and the polymeric binder to further improve the sensitivity of the sensing material. In some cases, the reactive chemistry additive can be added to the particulate carbon and the sensing material can contain the particulate carbon and no polymeric binder. Inset 990 shows schematics of graphene sheets 992 and the porous 3-dimensional structure 994 of the particulate carbon in the sensing material 950. Some non-limiting examples of the structured particulate conducting phase can contain 3-dimensionally structured microporous or mesoporous graphene-containing particles, or the particulate carbon described herein. Some non-limiting examples of polymeric binder include PEUT, PECH, PIB, and alkyl cellulose. Such structures are beneficial to detect analyte species and concentration in resonant gas sensors because they produce characteristic, reversible impedance responses that can be measured, or transduced, with a high frequency, resonant, antenna element.

Figure 9F:
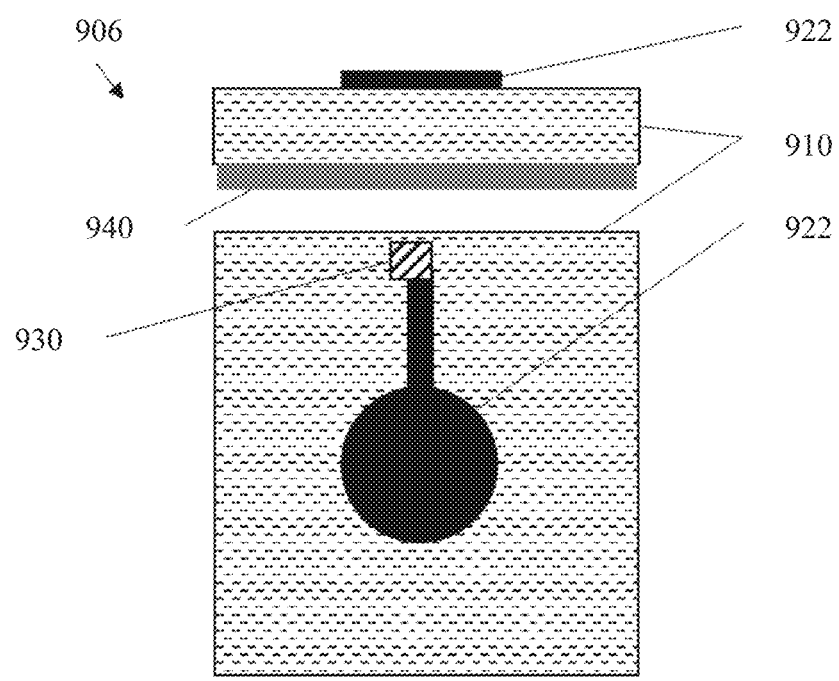
FIG. 9F shows a non-limiting example of a resonant gas sensor in side view and plan view, in accordance with some implementations.

FIG. 9F shows a non-limiting example of a resonant gas sensor 906 in side view and plan view, including a substrate 910, a transducer 922, a microprocessor 930, a ground electrode 940, and a sensing material, which can be incorporated into the substrate, one or both electrodes, or as a separate layer in the device. The resonant gas sensor 906 contains similar elements to those in resonant gas sensor 900, however, the transducer 922 in this example is a patch antenna in the shape of a circle, which is electrically coupled to a first terminal of the microprocessor, rather than a spiral antenna. The ground plane is formed from ground electrode 940 on the opposite side of substrate 910 and is coupled to a second terminal of the microprocessor through a via in the substrate, not shown in the figure.

The substrate 910 in this example contains the sensing material. In this example, the sensing material 950, such as a PEUT, PECH, PIB, and alkyl cellulose, is sensitive to an analyte, such that when the resonant gas sensor 906 is exposed to the analyte, the frequency response of the resonant circuit formed form the transducer 922 and the sensing material 950 changes, and the response detected at the microprocessor 930 changes indicating the detection of the analyte. Similar to the examples shown in FIGS. 9A, 9C and 9D, the response can either be reflected from the patch antenna transducer 922 back to the first terminal of the microprocessor, or be transmitted through the patch antenna transducer 922 and be detected at the second terminal of the microprocessor, connected to the ground electrode 940.

The resonant gas sensors described in FIGS. 9A, 9C, 9D and 9F are non-limiting examples only, and many other variations exist. For example, the electrodes, transducers, capacitive elements and/or substrates can contain sensing material in any of the above examples. In such examples, the sensing material itself can be patterned to affect the resonant frequencies of the gas sensor circuit. Additional elements can also be added, for instance, to provide additional sensing materials that can affect the response from the circuits in the above examples. The electrodes, transducers, capacitive elements and/or substrates in any of the above examples can contain the particulate carbon described herein. The electrodes, transducers, capacitive elements and/or substrates can be formed in many different shapes as well. For example, the transducers can be rectangular spiral antennas, such as shown in FIGS. 9A, 9C and 9D, square spiral antennas, ovular spiral antennas, or other types of spiral antennas.

The patch antenna transducers can be circular, such as shown in FIG. 9F, rectangular, square, ovular, or other patch-like shapes. Other transducer shapes are also possible, such as patterns that are resonant at particular frequency ranges. In some cases, more than one transducer can be driven by a single microprocessor, and multiple signals from the circuits containing the multiple transducers can also be detected by a single microprocessor. The circuits can also contain waveguides, such as microstrip lines, instead of simple electrical connections, such as shown in FIGS. 9A, 9C, 9D and 9F, to conduct the AC signals between elements in the gas sensor circuits. The geometry of the waveguides can be designed such that there is low loss of the AC signals between elements in the circuits. The capacitive elements can also be different types than that shown in FIG. 9D. For example, a 3-dimensional capacitor can be formed with structured electrodes surrounding a sensing material, to further increase the surface area of the capacitor and further improve the capacitance change upon exposure to an analyte. The circuits also can be electrically coupled by direct connections, such as shown in FIGS. 9A, 9C, 9D and 9F, or can be coupled through a dielectric material, since the AC fields can extend outside of a waveguide or other resonant structure.

The transducers used in the gas sensors described herein are one or more of the antennas or transducers described in U.S. application Ser. No. 15/944,482, entitled "Microwave Chemical Processing," which is assigned to the same assignee as the present application, and is incorporated herein by reference as if fully set forth herein for all purposes.

The present resonant gas sensors can be modular, and a portion of the resonant gas sensor can be removed and replaced without the need to replace the entire resonant gas sensor. For example, a first portion of the resonant gas sensor including a sensing material can be removed and replaced with a new first portion containing fresh sensing material, and a second portion of the resonant gas sensor including a transducer, electrodes and a microprocessor can be left intact and not be replaced. This can be advantageous, for example, in situations where the sensing material has a shorter shelf life than the other components of the resonant gas sensor, such as the transducer and/or microprocessor, or in situations where the sensing material can become damaged or soiled after prolonged use.

Figure 9G:
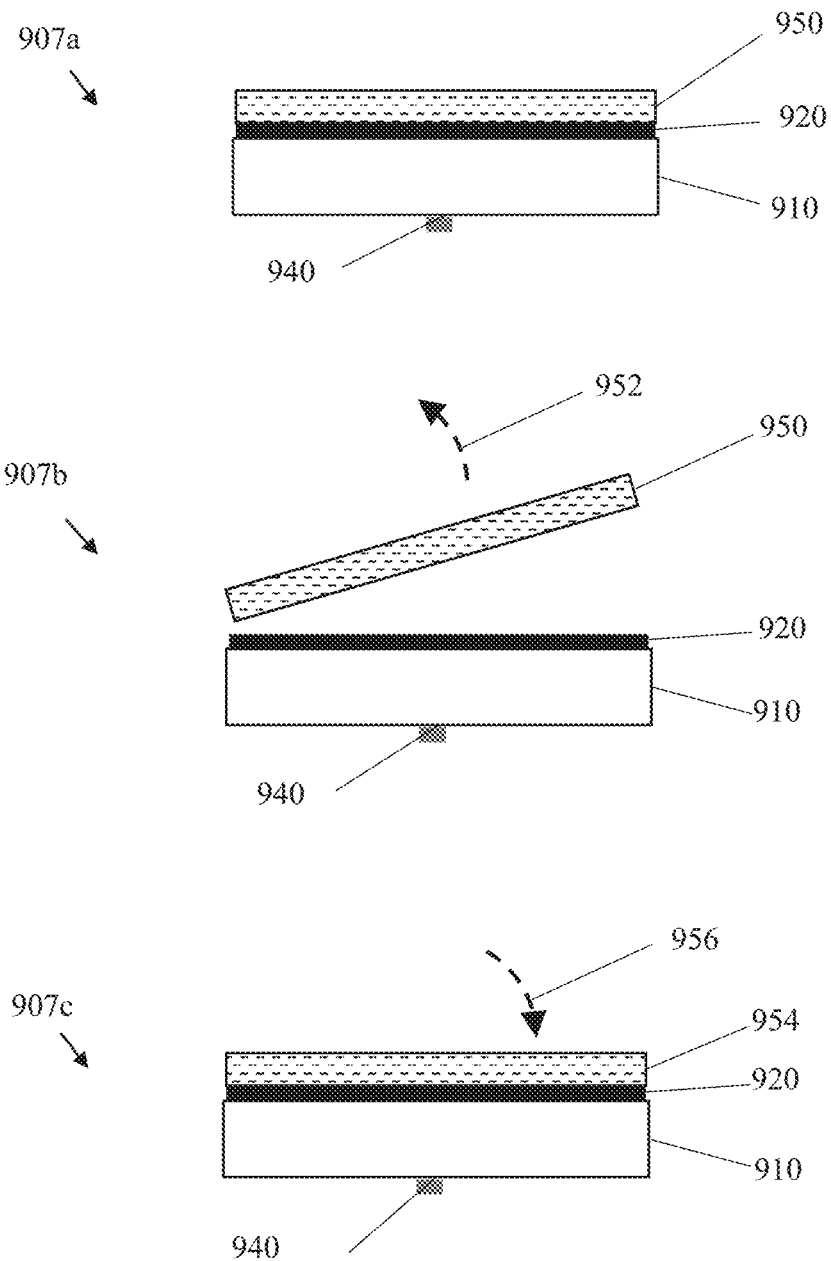
FIG. 9G shows a non-limiting example of a resonant gas sensor in side view, in accordance with some implementations.

FIG. 9G shows a non-limiting example of a resonant gas sensor 907 from an inside view, including a substrate 910, a transducer 920, a microprocessor, not shown, a ground electrode 940, and a sensing material 950. The resonant gas sensor 907a is similar to the resonant gas sensor 902 in FIG. 9C, and the sensing material 950 is disposed above successive loops of the spiral transducer 920 and other electronics such as the microprocessor, as shown in the side view and plan view in FIG. 9C. FIG. 9G illustrates that the sensing material 950 can be designed to be removable, as shown in resonant gas sensor 907b where action arrow 952 shows sensing material 950 being removed. Then, a new sensing material 954 can be attached to the resonant gas sensor 907c, as shown by action arrow 956. For example, the sensing material can be equipped with an adhesive on the surface that is adjacent to the transducer 920, such that when a force is applied, such as shown by action arrow 952, the sensing material 950 can be removed from the resonant gas sensor 907b. And, likewise the new sensing material 954 can have an adhesive on the surface such that when a force is applied, such as shown by action arrow 956, the new sensing material can be affixed onto the transducer 920.

There are multiple layers of sensing material, such as 950 in FIG. 9G, stacked on top of each other, and when the top layer of sensing material degrades or is no longer needed, then the top layer can be removed and the next fresh layer of sensing material is exposed.

Gas sensors with replaceable portions are printed on a substrate, and the sensing material and associated electronics, such as microprocessors and transducers, are contained on the substrate. This configuration can be advantageous to affix a stand-alone gas sensor to an object, such as a shipping package or a packaged product. Some parts of a gas sensor with replaceable portions can be printed on a substrate, and other parts are integrated with another piece of hardware, such as a scale to weigh packages, or the interior of a vehicle, and the printed parts are affixed to the parts that are integrated with another piece of hardware. This configuration can be advantageous to reduce the cost of the gas sensor over time and increase the lifetime of the gas sensor, since the sensing material can be replaced when soiled or damaged without replacing the associated electronics, which are still functional.

The resonant gas sensor with a replaceable portion shown in FIG. 9G is only one non-limiting example, and resonant gas sensors with other designs can benefit from a similar replaceable portion, such as containing the sensing material. For example, the capacitive element 960 including sensing material 950 in resonant gas sensor 904 in FIG. 9D can be replaceable, and the other components, such as microprocessor 930 and transducer 920, can be non-replaceable. In another example, the sensing material 950 in resonant gas sensor 904 in FIG. 9D can be replaceable, and the electrodes for the capacitive element 960 can be arranged under the sensing material such that the capacitive element 960 and other components, such as microprocessor 930 and transducer 920, can be non-replaceable.

Figure 10A:
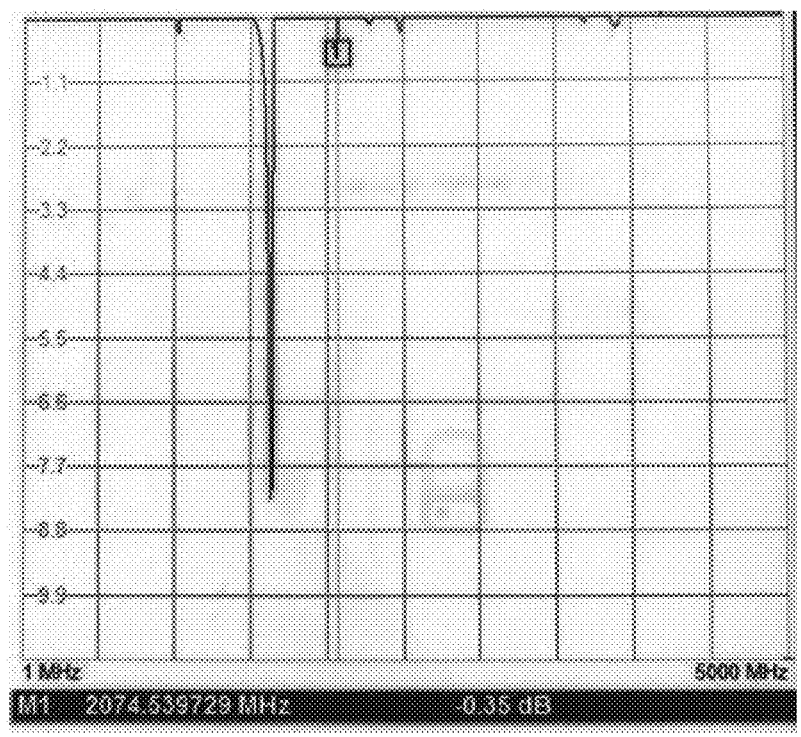
FIGS. 10A-10C show a time evolution of example spectra produced when an analyte is detected by a resonant gas sensor, in accordance with some implementations.
Figure 10B:
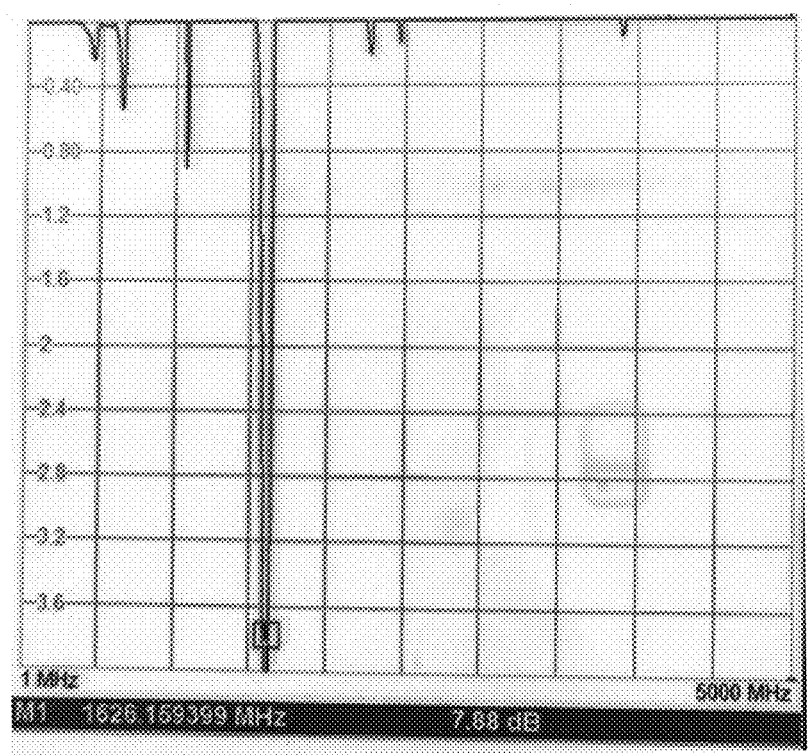
Figure 10C:
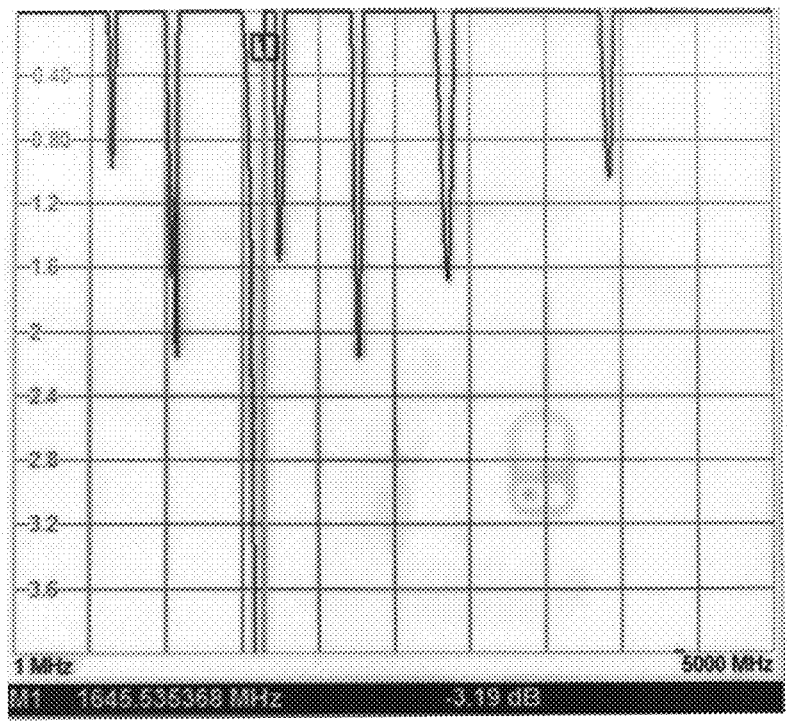

FIGS. 10A-10C show a time evolution of example spectra produced when an analyte was detected by a resonant gas sensor similar to that shown in FIG. 9D, but the system in this example used a separate virtual network analyzer rather than an integrated microprocessor. The resonant gas sensor in this example contained a substrate that was paper with a silica layer deposited on the surface, and a printed spiral transducer and capacitive element connected in parallel. The capacitive element contained a sensing material with the particulate carbon described herein and a dielectric polymer, such as PEUT. The analyte in this example is isopropyl alcohol mixed with acetone and water. FIGS. 10A, 10B and 10C show the reflected signal, such as S11, from the circuit after about 1-2 seconds, about 15 seconds and about 30 seconds, respectively. In the absence of any analyte the signal is a flat line with no features at 0 dB. FIG. 10A shows some evidence that an analyte is present after only about 1-2 seconds. Therefore, the design and materials of the resonant gas sensor in this example enable a fast detection of an analyte. FIG. 10C shows multiple peaks representative of the analyte detected and illustrates the capability of this type of resonant gas sensor to identify a species of analyte, such as by comparing a detected spectrum with those in a stored library.

The AC signals used by the resonant gas sensors described above contain a set of frequencies, such as in a range from 1 MHz to 20 GHz, and the method by which the signal is applied can vary. For example, a single frequency sweep can be performed continuously, or periodically at various intervals, such as once every 1 second, 10 seconds, 1 minute, 10 minutes, or once an hour. In some cases, different sweeps with different resolutions, such as frequency spacing between the different frequencies within a range can be performed at different intervals.

In one non-limiting example, a first coarse sweep is performed followed by targeted sweeps. Other similar methods for supplying different frequencies to a resonant gas sensor are also possible. In this example, a first fast/coarse sweep of the frequency range is performed by the microprocessor, and a peak is detected. After the first coarse sweep, the microprocessor can drive the resonant sensor to the peak and dither around it to ascertain the peak frequency and relative intensity values more accurately. Ascertained peak values can be compared to a library of possible analytes, and in some cases, if the library indicates a possible match, the microprocessor can be used to sweep to a second peak in the spectrum of a possible analyte to obtain a second indicator as a check to reduce the number of false positives.

The peak values, and/or other features of measured spectra, are compared to a library of possible analytes using an integrated microprocessor, such as shown in FIG. 9A, 9C, 9D or 9F, or communicating with a remote processor and/or database. Such a method containing a first coarse scan followed by targeted subsequent dither scans can be beneficial to provide high detection accuracy with lower power requirements than performing a fine scan over a large set of potential analyte resonant frequencies. To further save power, such a method can be performed periodically, such as once every 1 second, 10 seconds, 1 minute, 10 minutes, or once an hour. The system requirements can be relaxed to further save cost and power by targeting a +/−20% accuracy level for the concentration of a measured analyte. Although such a system may not provide highly accurate concentrations, it can have low power requirements, such as less than 1 nW, or less than 1 pW, and have a low production cost, such as less than 1 US dollar per unit, or less than 5 US dollars per unit, depending on the complexity of the system and the number of analytes capable of being detected, and therefore still be useful in many applications where indication and detection of an analyte are needed and an accurate concentration measurement is not required, such as to detect the presence of an explosive inside of a mailed package, or detecting the occurrence of food spoilage in a packaged food product.

Sensor Systems

Figure 11:
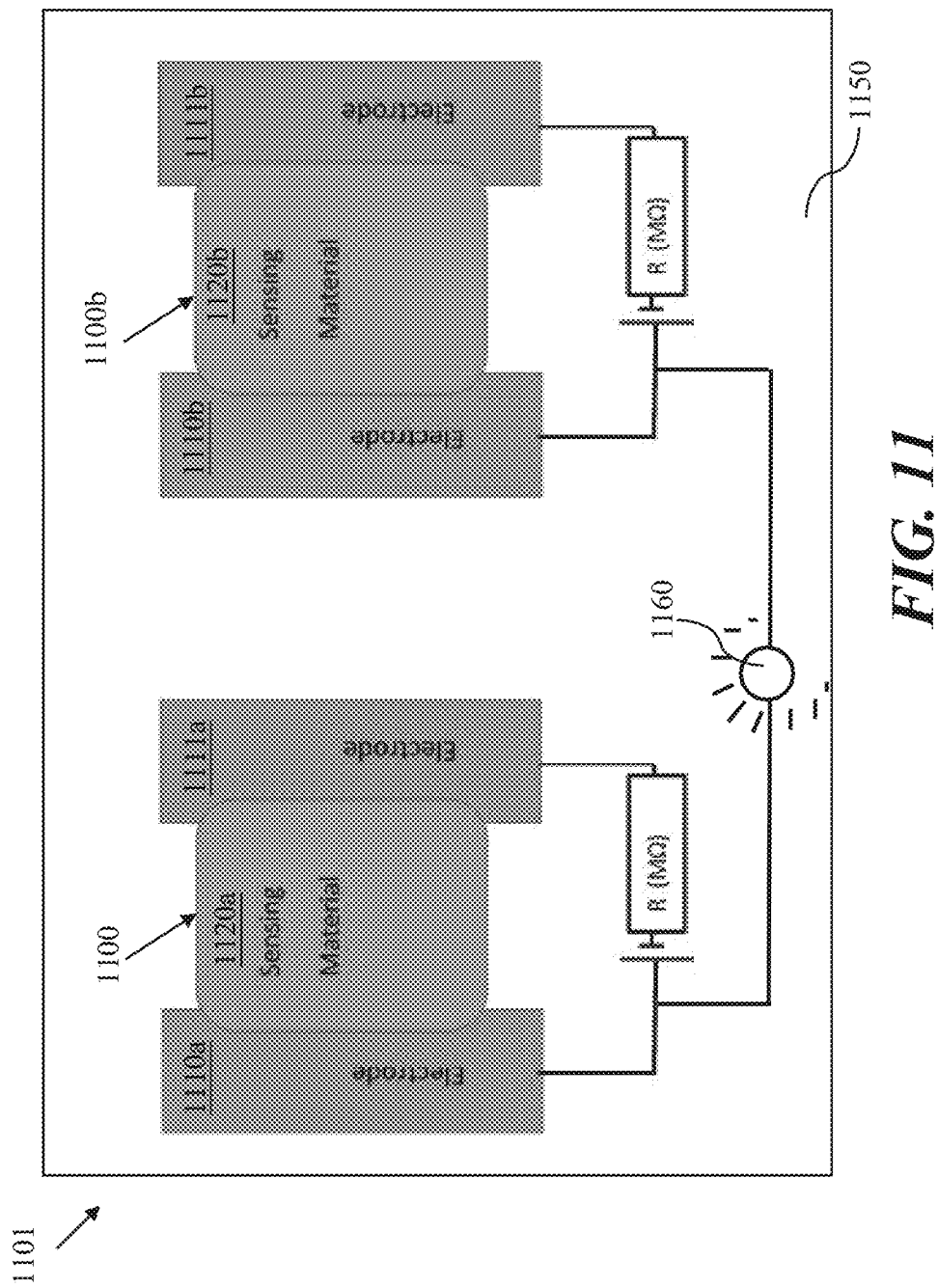
FIG. 11 shows a non-limiting example of a sensor system in which multiple individual chemical sensors are used for detecting an analyte, in accordance with some implementations.

FIG. 11 shows an example of a sensor system 1101 in which multiple individual gas sensors are used for detecting one or more chemical compounds, such as various analytes. Sensor system 1101 includes a first sensor 1100a for detecting a first target chemical, and a second sensor 1100b for detecting a second target chemical. Here, both first sensor 1100a and second sensor 1100b are electrochemical sensors, but other types of sensors, described herein, can also be used.

For example, the gas sensors of the sensor system may be electrochemical, high frequency, resonant, or a combination of these. In some cases, first sensor 1100a and second sensor 1100b are printed on the same substrate 1150, such as a label. Each sensor 1100a, 1100b can include a first electrode 1110a, 1110b, respectively, a second electrode 1111a, 1111b, respectively, and an electrolyte 1120a, 1120b, respectively, where the components include particulate carbon and redox mediators as described in relation to FIG. 11. Although two sensors 1100a and 1100b are shown in this example, more than two sensors can also be included. An array of sensors can be used to add functionality, such as the ability to detect multiple gases, subtract a background level of moisture and/or improve the sensitivity to an analyte. Furthermore, other non-printed sensors, such as IR sensors, can be included. As one example, an IR sensor can be included to detect $NO_2$ groups.

An indicator 1160 is coupled to sensors 1100a and 1100b through electrical circuitry (not shown), where both sensors 1100a and 1100b must positively sense detection of their target chemical for the indicator 1160 to be activated. The combination of all the individual target substances being present indicates that a certain compound is present. Types of indicators 1160 that may be used include an optical indicator, such as a light emitting diode, an acoustic output, or a visual display such as a text or graphic read-out. The indicator 1160 can be part of the sensor devices, such as if the individual sensors themselves can provide a positive indication of detection through a color change of the sensing material, or other indicator mechanism. The sensor system 1101 represents examples in which the presence of multiple sensors in one device are utilized to detect a combination of chemicals, to characterize an overall compound. The presence of multiple sensors can also help rule out false positives.

In the sensor systems for detecting a chemical compound, such sensor systems can include a first sensor configured to detect a first target chemical, a second sensor configured to detect a second target chemical that is different from the first target chemical, and a substrate on which the first sensor and the second sensor are printed. An indicator indicates when both the first sensor positively detects the first target chemical and the second sensor positively detects the second target chemical.

Additionally, other components can be integrated with the gas sensors to add functionality to a gas sensors system. Some non-limiting examples of electro-active labels containing the present gas sensors, that also contain a display-based human/machine interface are devices that can display telemetry, Q-codes or bar codes, and/or icons. Example scenarios include telemetry, where information can be updated, and/or have an image such as a gage; a Q-code (QR code) or bar code, using digital data or number/text formats; and icons for packages where a color or image change is displayed. In these various scenarios, a change in the display, such as in the symbol or color, or a back-and-forth change, can be used to indicate the condition of the product.

These display telemetry devices are a new approach to providing information about the contents of a package status, using a microprocessor-based machine and user detection of the conditions within a package. The present devices can also optionally include low power communications components, such as to communicate directly with other electronic devices.

In a non-limiting example, a cardboard shipping box was equipped with an electrochemical sensor, a resonant sensor similar to that shown in FIG. 9D, integrated microprocessors to drive the sensors and detect signals from the sensors, a display to communicate visual information, such as a species of analyte detected, and a wireless communication chip, such as a Wi-Fi chip, to communicate information to other devices. The electronics were powered by an integrated battery.

The sensing material in the electrochemical sensor and the resonant sensor in this example were both printed, and both contained the particulate carbon described herein. The beneficial properties of the particulate carbon coupled with the sensor designs enabled them to utilize low power, such as with currents from 0.1 microamps to 5 microamps, to detect analyte species. This example illustrates that gas sensors utilizing the particulate carbon described herein can be produced using low cost low power driver/detection electronics that can be integrated into a small package. Furthermore, this example showed that such low cost printed gas sensors can also be integrated with other system components such as displays and communication chips.

Figure 12:
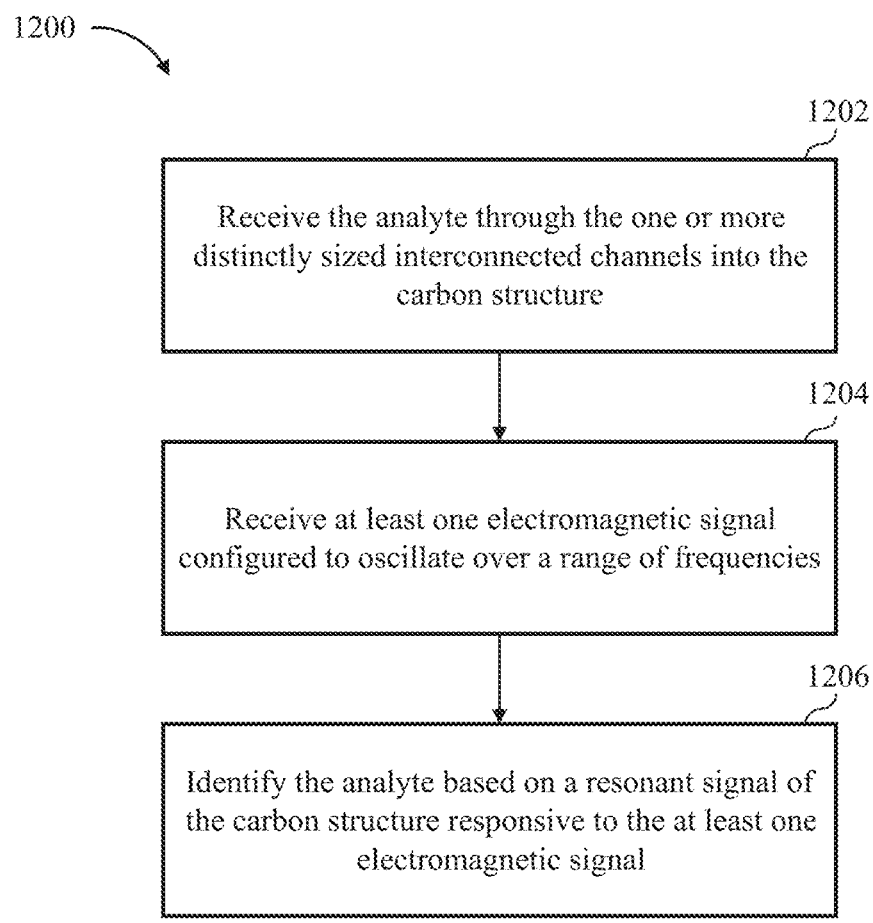
FIG. 12 shows a method for detecting an analyte in a sensing material defined by a carbon structure including a plurality of distinctly sized interconnected channels, in accordance with some implementations.

A method 1200 is shown in FIG. 12 for detecting an analyte in a sensing material defined by a carbon structure including a plurality of distinctly sized interconnected channels. The method can include one or more operations including receiving the analyte, at block 1202, through the one or more distinctly sized interconnected channels into the carbon structure; receiving, at block 1204, at least one electromagnetic signal configured to oscillate over a range of frequencies; and, identifying, at block 1206, the analyte based on a resonant signal of the carbon structure responsive to the at least one electromagnetic signal. A frequency of a peak in the resonant signal induced by dithering the at least one electromagnetic signal can indicative of a presence of the analyte in the sensing material.

The gas sensors described herein can be integrated into a product or package, such as on a cardboard box, or food package. The gas sensors described herein can be placed adjacent to a product or package and can detect analytes on or within the product or package. For example, a gas sensor can be integrated into or placed adjacent to a scale that is used to weigh shipping containers, and the gas sensor can be used to detect analytes on or within any shipping package being weighed by the scale. As another example, a gas sensor can be integrated into or placed adjacent to a component of a vehicle that is used to transport shipping containers, such as within a mail truck, and the gas sensor can be used to detect analytes on or within any shipping package being transported by the vehicle. As still further examples, a gas sensor can be integrated into a conveyor belt or mounted onto a portion of a mechanical conveyance device. Additionally, or alternatively, a gas sensor can be integrated into handling equipment, such as a robot arm, or handling apparel, such as gloves, etc., and the gas sensor can be used to detect analytes on or within any shipping package being conveyed or handled.

A fan, or a suction device, such as a vacuum pump, is used to direct environmental gasses, such as possibly containing an analyte, towards the present gas sensors and/or into an enclosure containing the present gas sensors. For example, the gas sensor can be placed into an enclosure, and a fan or vacuum pump is used to draw the surrounding environmental gasses into the enclosure, such that the flow effectively exposes the gas sensor to the analyte. In another example, a gas sensor is placed adjacent to a set of objects, such as shipping packages, mousepads, or other products, to be monitored for an analyte and a fan (or set of fans) is used to draw the analyte from the objects and direct the analyte onto the gas sensor.

Printing of Chemical Sensors

Gas sensor components, such as electrodes and sensing materials, are printed from carbon-based inks, such as containing the particulate carbons describe herein. The electrical components of the present gas sensors can be printed on backing materials such as labels and integrated with other hardware components on a substrate. More than one sensor can be printed on the same substrate, such as multiple sensors of the same type, or different types of sensors, such as electrochemical, high frequency, chemiluminescent. Types of substrates—which also may be referred to as backing materials—include rigid or flexible substrates, card stock, labels, or other types of materials used for printing.

Printed gas sensor components containing the particulate carbon described herein are further processed after printing to increase the conductivity of the printed components. For example, particulate carbon containing electrodes, transducers, and/or capacitive elements of the resonant gas sensors described herein can be further processed after initial printing to increase the conductivity of these printed components. The transducers described herein require high conductivities, such as greater than 3,500 S/m, or greater than 5,000 S/m, or greater than 10,000 S/m, for example, in order to perform as effective transducers, and in some cases these conductivities cannot be reached using printed particulate carbon without further processing. Some non-limiting examples of processes to improve the conductivity of printed particulate carbon materials are sintering and/or calendaring. For example, sintering can be performed using a plasma, laser, or microwave energy. In some cases, the sintering process can locally heat the printed material and not substantially affect the substrate and/or other underlying materials. Calendering can be performed to increase the conductivity of the printed carbon materials. For example, calendering using a heated roller, or a roller equipped with an energy source, such as microwave energy, to sinter and calendar simultaneously can increase the conductivity of the printed particulate carbon.

High conductivity printed gas sensor components can be formed by printing a mixture of the present particulate carbon with other conductive particles added to increase the conductivity of the printed components. For example, the electrodes, transducers, and/or capacitive elements of the resonant gas sensors described herein can be formed using such mixtures. Some non-limiting examples of conductive particles that can be mixed with the particulate carbon described herein are Ag, Sn and/or Sb particles. Printed components for gas sensors containing the particulate carbon and additional conductive particles can be advantageous because the particulate carbon provides beneficial structure to the printed components, such as high surface areas, and the conductive particles improve the conductivity of the printed components.

The devices can be designed to operate in low power ranges, such as 0 to 1 volt, or less than 100 µW, or less than 1 µW. In some cases, the low power consumption is made possible by the high conductivity, the high surface area and mesoporous structure of the carbon-based materials used in printing the components, the small size of the devices, the choice of detection methodologies, and optionally the choice of display technologies. The overall device architecture may also use low power technology for the various system components, such as gas sensor and indicator.

The printed components are made from carbon-based inks and can be electrically coupled to each other and/or to one or more additional hardware components, which can be mounted on the substrate. The hardware components can be, for example, one or more of an output display, microcontroller units (MCU), switches, and capacitors, among others. The hardware components use information stored in, generated by, and/or communicated from the printed components, such as by processing or displaying data from the printed components. The present devices can also optionally include low power printed communications components.

In addition to the particulate carbon described herein, types of carbon materials for printed components can include, but are not limited to, graphene, graphenes, graphene-based materials, graphene oxide, reduced graphene oxide, graphite oxide, graphite intercalation compounds, graphite, graphene, carbon nano-onions, diamond, p-type diamond, n-type diamond, glassy carbon, amorphous carbon, activated carbon, carbon black and/or carbon nanotubes, sulfur-based carbons, such as sulfur melt diffused carbon, and carbons with metal, such as nickel-infused carbon, carbon with silver nanoparticles, graphene with metal. The printed components can be printed by, for example, screen printing or ink-jet printing.

Reference has been made to implementations of the disclosed invention. Each example has been provided by way of explanation of the present technology, not as a limitation of the present technology. In fact, while the specification has been described in detail with respect to specific implementations of the invention, it will be appreciated that those skilled in the art, upon attaining an understanding of the foregoing, may readily conceive of alterations to, variations of, and equivalents to these implementations. For instance, features illustrated or described as part of one implementation may be used with another implementation to yield a still further implementation. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only and is not intended to limit the invention.

What is claimed is:

1. A sensor configured to detect an analyte, comprising:
    an antenna disposed on a substrate;
    a sensing material disposed on the substrate and electrically coupled to the antenna, the sensing material comprising:
        a carbon structure including a multi-modal distribution of pore sizes that define a surface area including bonding sites configured to interact with one or more additives and the analyte, the carbon structure configured to generate a resonant signal indicative of one or more characteristics of the analyte in response to an electromagnetic signal, the carbon structure comprising:
            a plurality of distinctly sized interconnected channels defined by the surface area and configured to be infiltrated by the analyte; and
            a plurality of exposed surfaces configured to adsorb the analyte.

2. The sensor of claim 1, wherein each of the one or more distinctly sized interconnected channels includes at least one of microporous pathways or mesoporous pathways.

3. The sensor of claim 2, wherein each of the microporous pathways or mesoporous pathways is configured to increase a responsiveness of the sensing material proportionate to an amount of the analyte within the carbon structure.

4. The sensor of claim 1, wherein the sensing material is integrated into the antenna or positioned within a vicinity of the antenna.

5. The sensor of claim 1, wherein one or more characteristics of the resonant signal are indicative of a presence of one or more known harmful substances in the sensing material.

6. The sensor of claim 5, wherein the indication is based on a comparison of the one or more characteristics of the resonant signal with one or more characteristics of the known harmful substances.

7. The sensor of claim 1, wherein the sensing material is configured to oscillate at:
  a first amplitude at one or more resonant frequencies of the sensing material; and
  a second amplitude at one or more non-resonant frequencies of the sensing material, wherein the first amplitude is greater in magnitude than the second amplitude.

8. The sensor of claim 1, further comprising a pair of electrodes electrically coupled to a dielectric and the sensing material.

9. The sensor of claim 8, wherein the sensing material and the dielectric are positioned between the pair of electrodes and comprise a tank circuit.

10. The sensor of claim 1, wherein the carbon structure is at least partially bound by a polymer.

11. The sensor of claim 10, wherein the polymer comprises one or more polymer additives configured to alter electrical properties of the sensing material by interacting with the analyte.

12. The sensor of claim 1, wherein the carbon structure includes one or more tuned materials configured to increase a resonance sensitivity of the sensing material across one or more frequency ranges.

13. The sensor of claim 1, wherein the carbon structure further comprises a plurality of three-dimensionally (3D) structured aggregates, each aggregate of the plurality of 3D structured aggregates including a plurality of nanoparticles.

14. The sensor of claim 13, wherein the 3D structured agglomerates are configured to generate an impedance response indicative of one or more characteristics of the sensing material based on an excitation signal.

15. The sensor of claim 1, wherein the sensing material is configured to generate one or more resonant signals indicative of a type of the analyte based on an electromagnetic signal.

16. A sensor system configured to detect an analyte, comprising:
  a substrate; and
  a resonant circuit configured to be removed without requiring replacement of the substrate, the resonant circuit disposed on the substrate and comprising:
    an antenna disposed on the substrate;
    a sensing material disposed on the substrate and electrically coupled to the antenna, the sensing material comprising:
      a carbon structure including a multi-modal distribution of pore sizes that define a surface area including bonding sites configured to interact with one or more additives and the analyte, the carbon structure configured to generate a resonant signal indicative of one or more characteristics of the analyte in response to an electromagnetic signal, the carbon structure comprising:
        a plurality of distinctly sized interconnected channels defined by the surface area and configured to be infiltrated by the analyte; and
        a plurality of exposed surfaces configured to adsorb the analyte.

17. The sensor system of claim 16, wherein the analyte is configured to be at least partially contained within a package.

18. The sensor system of claim 16, wherein the resonant circuit is attached to the antenna by compression.

19. The sensor system of claim 16, wherein degradation of a removable top layer of the sensing material is indicative of a need for replacement of the removable top layer.

20. The sensor system of claim 16, wherein the resonant circuit is configured to detect the analyte flowing from a vehicle.

21. The sensor system of claim 16, wherein the resonant circuit comprises a capacitive element that at least partially contains the sensing material.

22. The sensor system of claim 21, further comprising a pair of electrodes electrically coupled to the capacitive element.

23. The sensor system of claim 16, further comprising a circuit configured to generate the electromagnetic signal.

24. The sensor system of claim 23, wherein a frequency of a peak in the resonant signal induced by dithering the electromagnetic signal is indicative of a presence of the analyte in the sensing material.

25. The sensor system of claim 24, further comprising a circuit configured to determine a presence of the analyte in the sensing material based on a comparison between the frequency of the peak in the resonant signal and one or more frequencies indicative of harmful substances.

26. A method for detecting an analyte in a sensing material defined by a carbon structure including a plurality of distinctly sized interconnected channels, the method comprising:
  receiving the analyte through the one or more distinctly sized interconnected channels into the carbon structure;
  receiving at least one electromagnetic signal configured to oscillate over a range of frequencies; and
  identifying the analyte based on a resonant signal of the carbon structure responsive to the at least one electromagnetic signal, wherein a frequency of a peak in the resonant signal induced by dithering the at least one electromagnetic signal is indicative of a presence of the analyte in the sensing material.

* * * * *